US012251332B2

(12) United States Patent
Garlock

(10) Patent No.: US 12,251,332 B2
(45) Date of Patent: Mar. 18, 2025

(54) REUSABLE URINE COLLECTION AND STORAGE SYSTEM

(71) Applicant: Advantage Urinal Systems, LLC, Bountiful, UT (US)

(72) Inventor: Larry Garlock, Bountiful, UT (US)

(73) Assignee: Advantage Urinal Systems, LLC, Bountiful, UT (US)

( * ) Notice: Subject to any disclaimer, the term of this patent is extended or adjusted under 35 U.S.C. 154(b) by 0 days.

(21) Appl. No.: 18/733,168

(22) Filed: Jun. 4, 2024

(65) Prior Publication Data

US 2024/0315866 A1 Sep. 26, 2024

Related U.S. Application Data

(62) Division of application No. 17/083,603, filed on Oct. 29, 2020, now Pat. No. 12,029,676.

(60) Provisional application No. 62/928,137, filed on Oct. 30, 2019.

(51) Int. Cl.
*A61F 5/451* (2006.01)
*A61F 5/44* (2006.01)
*A61F 5/441* (2006.01)

(52) U.S. Cl.
CPC ............ *A61F 5/451* (2013.01); *A61F 5/4404* (2013.01); *A61F 5/441* (2013.01)

(58) Field of Classification Search
CPC ......... A61F 5/451; A61F 5/4404; A61F 5/441
See application file for complete search history.

(56) References Cited

U.S. PATENT DOCUMENTS

| | | | | |
|---|---|---|---|---|
| 1,440,765 A | * | 1/1923 | Buckley | A61F 5/44 4/144.1 |
| 2,382,276 A | * | 8/1945 | Wells | A61F 5/455 4/144.1 |
| 2,522,273 A | * | 9/1950 | Johnson | A61G 9/006 4/144.1 |
| 2,875,451 A | * | 3/1959 | Stegeman | A61G 9/006 4/144.1 |
| 3,070,810 A | | 1/1963 | Jones | |
| 3,231,901 A | | 2/1966 | Kennedy | |
| 3,259,920 A | | 7/1966 | Voller | |
| D213,408 S | | 2/1969 | Brodsky et al. | |
| 3,479,671 A | * | 11/1969 | Beich | A61G 9/006 4/144.1 |

(Continued)

FOREIGN PATENT DOCUMENTS

GB 2216010 10/1989

*Primary Examiner* — Guy K Townsend
(74) *Attorney, Agent, or Firm* — Thorpe North & Western, LLP

(57) ABSTRACT

A urine collection and storage system has a urinal and a remote collection bag interconnected by a tube. An intermediate coupler in the tube and adjacent to the urinal bifurcates the tube into separable proximal and distal portions. The proximal portion of the tube is shorter and stiffer while the distal portion of the tube is longer length and less stiff to provide both flexibility and resist kinking. The collection bag can have a pair of layers joined together about substantially a perimeter with a double seal including an outer seal adjacent the perimeter and an inner seal spaced-apart from the outer seal. A plurality of different reusable urine collection and storage kits can be provided with different urinals adapted for individuals.

20 Claims, 13 Drawing Sheets

(56) References Cited

U.S. PATENT DOCUMENTS

| | | | |
|---|---|---|---|
| 3,537,109 A | 11/1970 | Spurrier et al. | |
| 3,626,980 A * | 12/1971 | Svensson | F16K 15/16 |
| | | | 604/323 |
| 3,650,272 A | 3/1972 | Ericson | |
| 3,703,731 A | 11/1972 | Leiser | |
| 3,716,871 A * | 2/1973 | Borse | A61G 9/006 |
| | | | 4/144.2 |
| D245,267 S | 8/1977 | Gruber | |
| 4,050,103 A * | 9/1977 | Nakao | A61G 9/006 |
| | | | 4/144.3 |
| 4,059,124 A | 11/1977 | Hill | |
| 4,091,476 A * | 5/1978 | DeBurgh | A61G 9/006 |
| | | | 4/144.3 |
| 4,117,845 A * | 10/1978 | Brown | A61G 9/006 |
| | | | 4/144.1 |
| 4,121,306 A * | 10/1978 | Bringman | A61G 9/006 |
| | | | 600/576 |
| 4,189,789 A * | 2/1980 | Hofstetter | A61G 7/0503 |
| | | | 294/142 |
| 4,192,295 A | 3/1980 | Sherlock | |
| 4,202,057 A | 5/1980 | Ibarra | |
| 4,270,231 A | 6/1981 | Zint | |
| 4,360,933 A | 11/1982 | Kimura et al. | |
| D273,133 S * | 3/1984 | Babic | A61F 5/455 |
| | | | D24/117 |
| D274,469 S | 6/1984 | Huang et al. | |
| 4,457,314 A | 7/1984 | Knowles | |
| D277,410 S | 1/1985 | Floyd | |
| 4,568,339 A | 2/1986 | Steer | |
| D286,569 S | 11/1986 | Nakao et al. | |
| 4,631,061 A | 12/1986 | Martin | |
| D289,690 S | 5/1987 | Hanson | |
| 4,665,571 A * | 5/1987 | Muccione | A61G 9/006 |
| | | | 4/144.1 |
| D297,462 S | 8/1988 | Meunchen | |
| 4,769,858 A * | 9/1988 | Gamm | A61G 9/006 |
| | | | 215/384 |
| 5,010,599 A * | 4/1991 | Nilsson | A61F 5/4405 |
| | | | 4/144.2 |
| 5,331,689 A * | 7/1994 | Haq | A47K 11/12 |
| | | | 604/326 |
| 5,343,570 A * | 9/1994 | Arpaia | A61G 7/0503 |
| | | | 4/144.1 |
| D357,979 S * | 5/1995 | Evans | A61F 5/455 |
| | | | D24/122 |
| 5,551,097 A * | 9/1996 | Short | E03D 13/00 |
| | | | 4/144.1 |
| 5,676,296 A | 10/1997 | Masters | |
| 5,797,147 A * | 8/1998 | Young | A61G 9/006 |
| | | | 604/350 |
| D399,308 S * | 10/1998 | Garlock | A61F 5/455 |
| | | | D24/122 |
| D399,908 S | 10/1998 | Guzman, Sr. et al. | |
| 5,926,858 A * | 7/1999 | Heller | A47K 11/12 |
| | | | 4/144.1 |
| 6,021,530 A * | 2/2000 | Davis | A61G 9/006 |
| | | | 4/144.1 |
| 6,021,531 A * | 2/2000 | Kirko | A47K 11/12 |
| | | | 4/144.1 |
| 6,070,275 A * | 6/2000 | Garlock | A47K 11/12 |
| | | | 4/144.1 |
| 6,119,280 A * | 9/2000 | Rentsch | A61G 9/006 |
| | | | 4/144.1 |
| 6,163,892 A * | 12/2000 | Abbato | A61G 9/006 |
| | | | 4/144.1 |
| 6,212,691 B1 * | 4/2001 | Heberer | A47K 11/12 |
| | | | 4/144.1 |
| 6,446,274 B1 | 9/2002 | Horiuchi | |
| 6,543,064 B1 * | 4/2003 | Prall | A61G 9/006 |
| | | | 4/144.1 |
| 6,588,024 B2 * | 7/2003 | Koelliker | A61G 9/006 |
| | | | 4/144.1 |
| 6,602,230 B1 * | 8/2003 | Fisher | A61J 19/02 |
| | | | 604/317 |
| 6,684,414 B1 * | 2/2004 | Rehrig | A61G 9/006 |
| | | | 4/144.1 |
| 6,793,651 B1 * | 9/2004 | Bennett | A61F 5/4405 |
| | | | 604/328 |
| D497,981 S * | 11/2004 | Call | A61F 5/455 |
| | | | D23/302 |
| 6,941,587 B1 | 9/2005 | Fletcher | |
| 6,968,577 B1 | 11/2005 | Taft, Jr. | |
| 7,181,781 B1 | 2/2007 | Trabold et al. | |
| 7,325,256 B1 | 2/2008 | Pecinka | |
| D578,211 S * | 10/2008 | Maze | A61F 5/455 |
| | | | D24/122 |
| D619,246 S | 7/2010 | Hazeres | |
| 8,181,284 B1 * | 5/2012 | Parker | B60R 15/04 |
| | | | 4/301 |
| 8,357,105 B2 * | 1/2013 | Fontaine | A61B 5/208 |
| | | | 600/580 |
| 9,603,737 B2 * | 3/2017 | Jenkin | A47K 11/12 |
| 9,931,102 B1 * | 4/2018 | Studer | A61B 10/007 |
| 10,258,532 B2 * | 4/2019 | Killian | A47K 11/12 |
| 10,568,473 B2 * | 2/2020 | Le | A61F 5/451 |
| 12,029,676 B1 * | 7/2024 | Garlock | A61F 5/453 |
| 2008/0250554 A1 * | 10/2008 | Smith | A61F 5/453 |
| | | | 4/144.2 |
| 2009/0249532 A1 * | 10/2009 | Smith | B60R 15/04 |
| | | | 4/114.1 |
| 2016/0095479 A1 * | 4/2016 | Jenkin | B60R 15/04 |
| | | | 4/144.1 |
| 2017/0164795 A1 * | 6/2017 | Le | A61F 5/451 |
| 2020/0154960 A1 * | 5/2020 | Le | A47K 11/12 |
| 2020/0352774 A1 * | 11/2020 | Rabinowitz | A61F 5/453 |
| 2024/0315866 A1 * | 9/2024 | Garlock | A61F 5/453 |

* cited by examiner

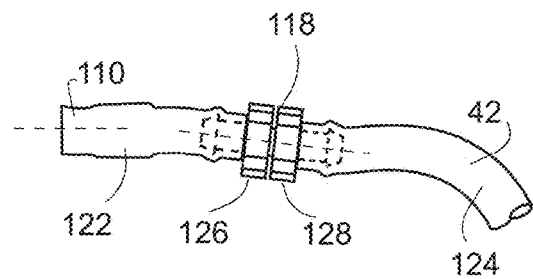
Fig. 3
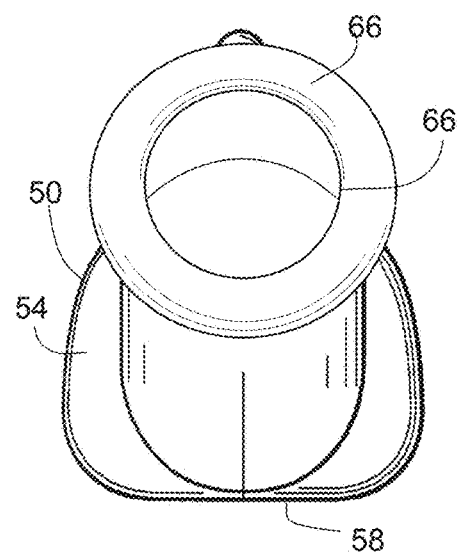
Fig. 4
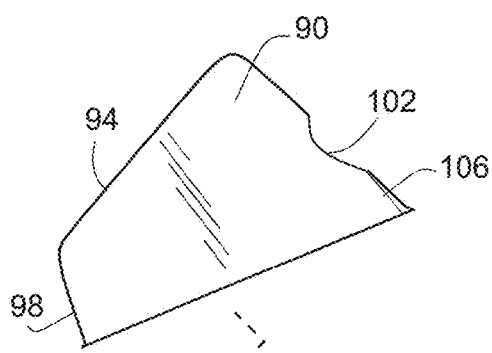
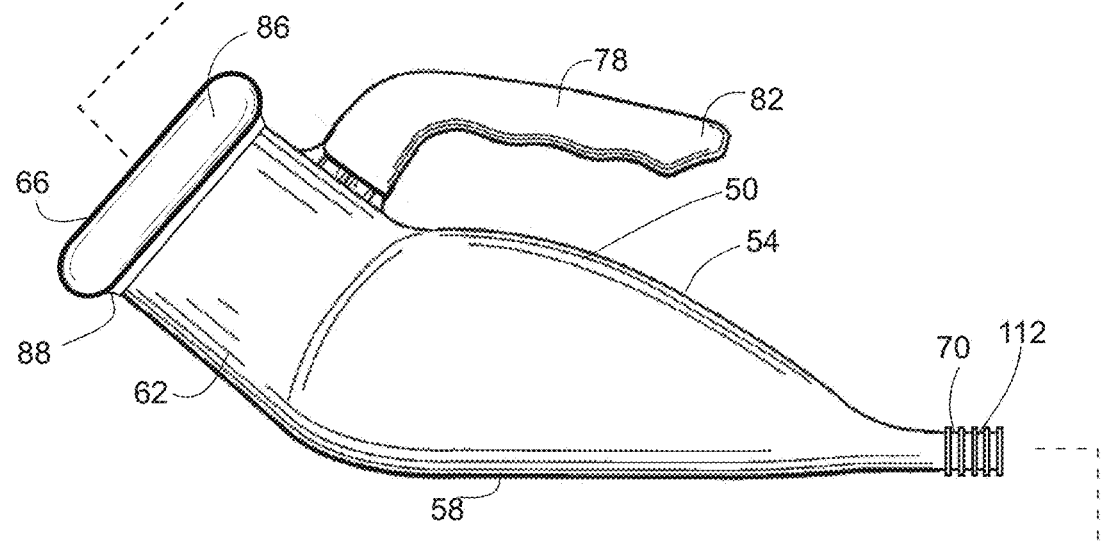
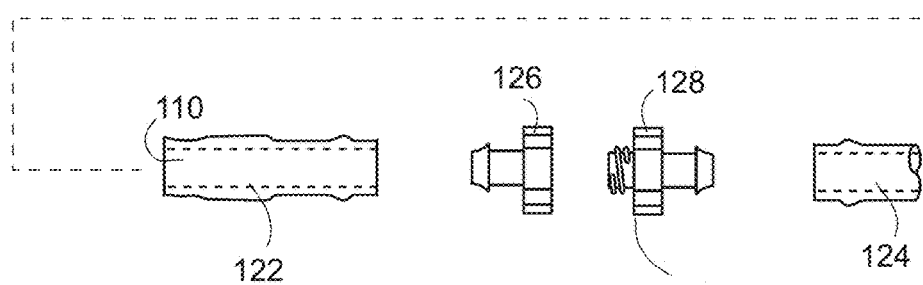
Fig. 2

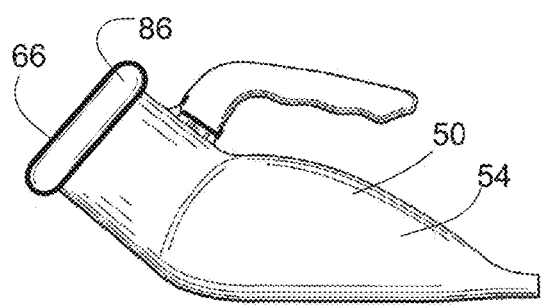
adult male, e.g. white
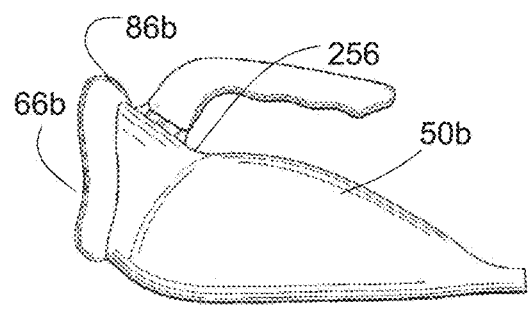
adult female, e.g. white
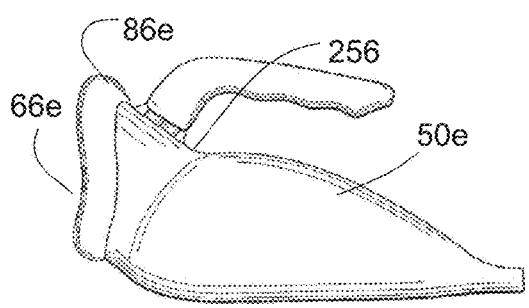
retracted male, e.g. grey
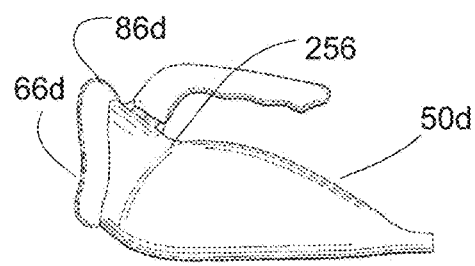
juvenile female, e.g. pink
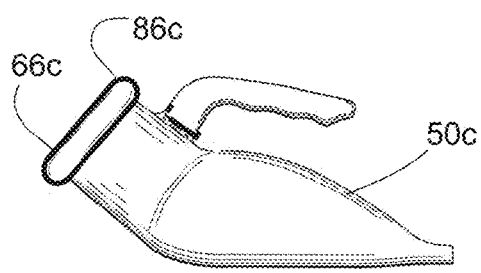
juvenile male, e.g. blue
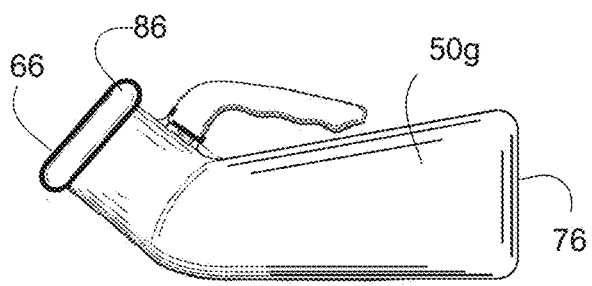
stand-alone
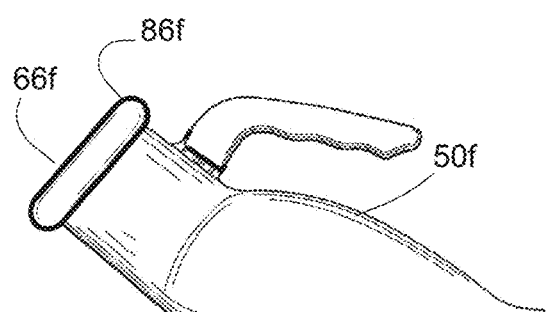
slim-fit, e.g. white
*Fig. 10*

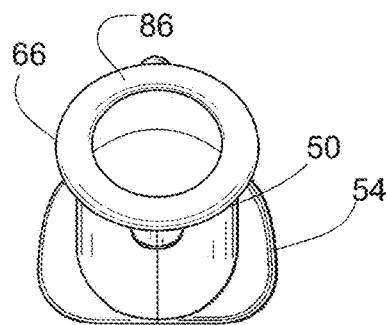
adult male, e.g. white
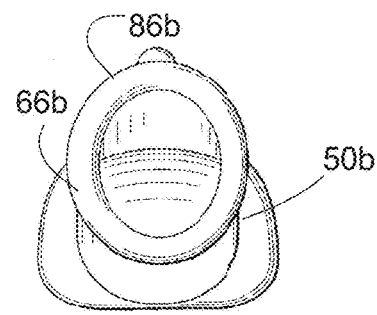
adult female, e.g. white
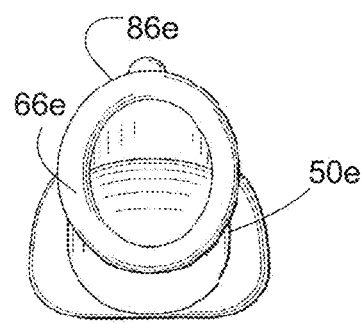
retracted male, e.g. grey
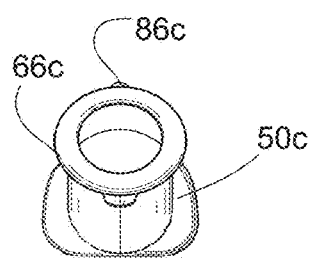
juvenile male, e.g. blue
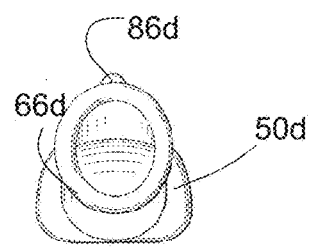
juvenile female, e.g. pink
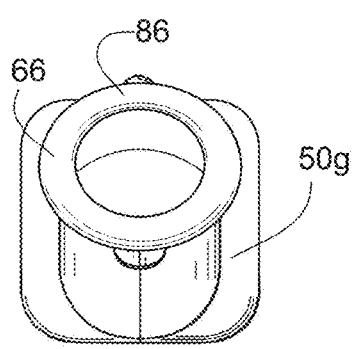
adult male, e.g. white
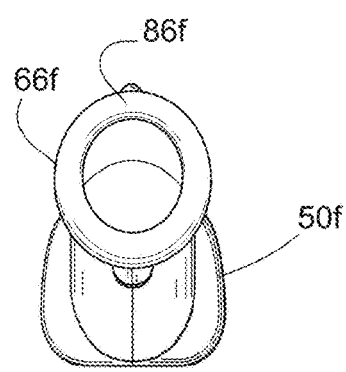
slim-fit, e.g. white
*Fig. 11*

REUSABLE URINE COLLECTION AND STORAGE SYSTEM

PRIORITY CLAIM

This is a divisional of U.S. patent application Ser. No. 17/083,603, filed Oct. 29, 2020, which claims priority to U.S. Provisional Patent Application Ser. No. 62/928,137, filed Oct. 30, 2019, which are hereby incorporated herein by reference.

BACKGROUND

Many people are bedridden or otherwise unable to ambulate in order to use a toilet. Many people also have difficulty ambulating, or should not be ambulating, in order to use a toilet. Falls from night-time toilet use can be a major source of falls. Urinary catheters, in which a tube is inserted through the urethra, have been used, but cannot be left in situ for long periods of time, can cause serious urinary tract infections, and can cause loss of bladder-memory. Portable urinals provide a plastic jug that can be temporarily position to receive urine. Such urinals are non-invasive, but can result in urine spills or falls due to urine spills. In addition, portable urinals can allow urine smell to permeate therefrom. Furthermore, portable urinals can be unsightly. The sight and smell of portable urinals can carry a stigma causing patients to shun their use.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein:

FIG. 2 is a partial exploded view of the urine collection and storage system of FIG. 1.

FIG. 3 is a partial side view of an intermediate coupler of the urine collection and storage system of FIG. 1.

FIG. 4 is a front view of a urinal of the urine collection and storage system of FIG. 1.

FIG. 10 is a schematic side view of urinals of the urine collection and storage system of FIG. 1.

FIG. 11 is a schematic front view of urinals of the urine collection and storage system of FIG. 1.

Figure 1:
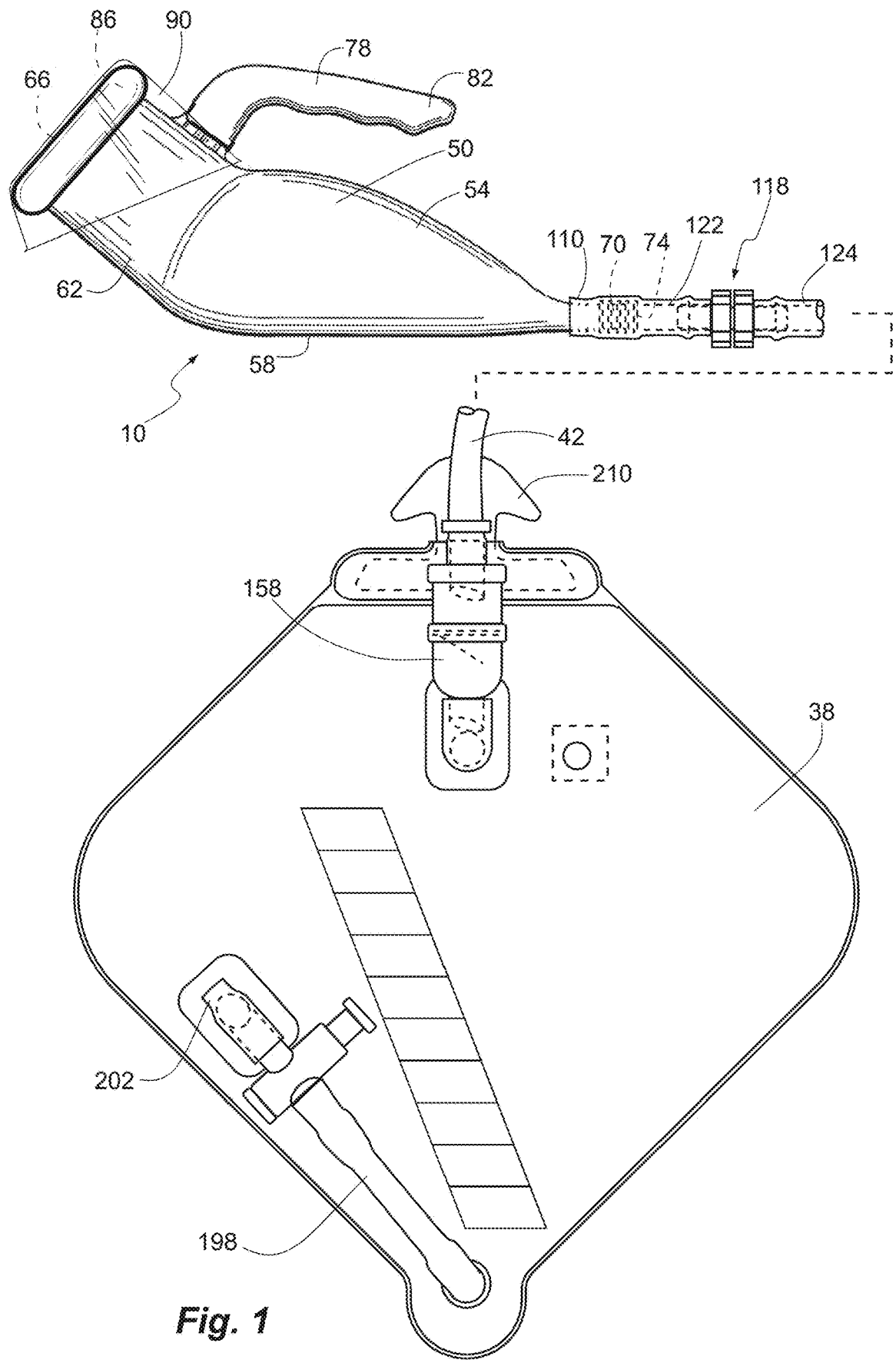
FIG. 1 is a schematic view of a urine collection and storage system in accordance with an example embodiment.

Reference will now be made to the exemplary embodiments illustrated, and specific language will be used herein to describe the same. It will nevertheless be understood that no limitation of the scope of the invention is thereby intended.

DETAILED DESCRIPTION

Before invention embodiments are disclosed and described, it is to be understood that no limitation to the particular structures, process steps, or materials disclosed herein is intended, but also includes equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence. Unless defined otherwise, all technical and scientific terms used herein have the same meaning as commonly understood by one of ordinary skill in the art to which this disclosure belongs.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order.

It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

The term "coupled," as used herein, is defined as directly or indirectly connected in an electrical or nonelectrical manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, the term "about" is used to provide flexibility to a numerical range endpoint by providing that a given value may be "a little above" or "a little below" the endpoint. It is understood that express support is intended for exact numerical values in this specification, even when the term "about" is used in connection therewith.

The terms "interference fit" and "friction fit" and "press-fit" are terms of art used interchangeably herein to refer to deliberately causing, increasing and/or using friction to deliberately resist movement. An interference fit or friction fit is different than and great than the existence of friction. While friction may exist between any two surfaces, is often desirable to do all one can to reduce this friction. An interference fit or friction fit can be distinguished from naturally occurring friction by being actually deliberately caused and increased. An interference fit can be created by dimensioning engaging parts so that their surfaces tightly bear against one another. A friction fit can be created by surface roughness that is rougher.

The term "gender" is used herein to refer to an individual's genitalia, with
male and female genitalia being different, and adult and juvenile genitalia being different, and even some genitalia deviating from normal due to medical conditions.

As used herein, a plurality of items, structural elements, compositional elements, and/or materials may be presented in a common list for convenience.

However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, sizes, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Furthermore, the described features, structures, or characteristics may be combined in any suitable manner in one or more embodiments. In this description, numerous specific details are provided, such as examples of layouts, distances, network examples, etc. One skilled in the relevant art will recognize, however, that many variations are possible without one or more of the specific details, or with other methods, components, layouts, measurements, etc. In other instances, well-known structures, materials, or operations are not shown or described in detail but are considered well within the scope of the disclosure.

An initial overview of the inventive concepts is provided below and then specific examples are described in further detail later. This initial summary is intended to aid readers in understanding the examples more quickly, but is not intended to identify key features or essential features of the examples, nor is it intended to limit the scope of the claimed subject matter.

The invention provides a urine collection and storage system that can reduce the risk of falls, decrease infections, decrease urine spills, reduce accidents, reduce smell, reduce stigmas, maintain bladder memory, and/or decrease excess or nighttime ambulation for those who are continent of bladder, but wheelchair or homebound or bedridden and require assistance with toileting. The urinal system comprises several types of urinals that are adapted to a user's gender, age and/or condition. Thus, an appropriate urinal can be provided. Tailoring the urinal for the user's gender and age can facilitate use and reduce stigma associated with use. In addition, the urinal systems are robust and adapted to avoid inadvertent leaking or spills. In addition, the urinal systems are adapted to reduce smell to further avoid stigma. Furthermore, the urinals are reusable and modular to extend lifetime.

The urine collection and storage system comprise a urinal to collect urine, a tube to convey urine from the urinal, and a collection bag to receive urine from the tube and temporarily store the urine. An intermediate coupler in the tube and adjacent to the urinal bifurcates the tube into separable proximal and distal portions. The proximal portion of the tube is shorter and stiffer while the distal portion of the tube is longer and less stiff to provide both flexibility and resist kinking. The collection bag can comprise a pair of layers joined together about substantially a perimeter to form a urine enclosure. In one aspect, each of the layers can have at least 28 mil thickness (0.028 in or 0.711 mm). In another aspect, the layers can be joined around substantially the entire enclosure with a double seal or weld. Thus, the collection bag can be less prone to rupture and leakage.

The system can also be configured to reduce odor. A removable cover can be disposed on the inlet of the urinal. An anti-reflux valve can be disposed between the collection bag and the tube.

In addition, a plurality of different reusable urine collection and storage kits can comprise: 1) an adult male system and urinal adapted for use by an adult male; 2) an adult female system and urinal adapted for use by an adult female; 3) a juvenile male system and urinal adapted for use by a juvenile male; 4) a juvenile female system and urinal adapted for use by a juvenile female; 5) a close-fit system and urinal for a retracted male; and 6) a slim-fit system and urinal for use by individuals with difficulty spreading his or her legs. Each of the plurality of kits comprises a urinal to collect urine, a tube to convey urine from the urinal, and a collection bag coupled to the tube to receive urine from the tube and to temporarily store the urine. Each of the kits also has a package containing the urinal, the tube, the collection bag and instructions for use. A stand-alone urinal can also be provided. A replacement collection bag and tube can also be provided.

Figure 12:
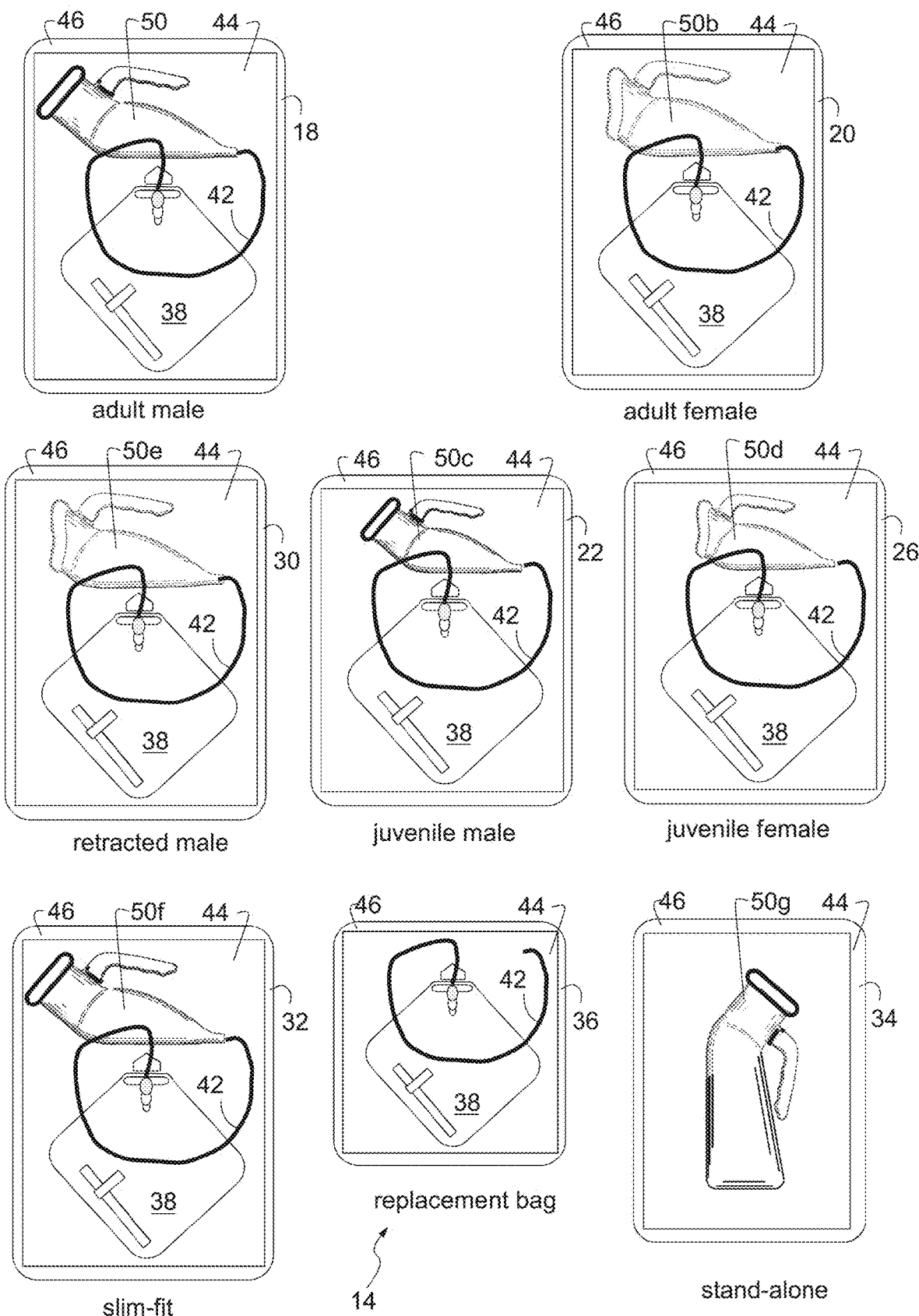
FIG. 12 is a schematic front view of a plurality of kits of the urine collection and storage system of FIG. 1.

As illustrated in FIG. 1, a urine collection and storage system 10 in accordance with the invention is shown. Referring to FIGS. 10-12, in one aspect, the system 10 can comprise a plurality of different reusable urine collection and storage kits 14, each with a urinal adapted for a particular user in order to provide a urinal adapted to a user's gender, age and/or condition. The plurality of kits 14 can comprise different types of kits with different urinals or components, including by way of example: 1) an adult male system or kit 18 adapted for use by an adult male; 2) an adult female system or kit 20 adapted for use by an adult female; 3) a juvenile male system or kit 22 adapted for use by a juvenile male; 4) a juvenile female system or kit 26 adapted for use by a juvenile female; 5) a close-fit system or kit 30 for a retracted male; and/or 6) a slim-fit system or kit 32 for use by individuals with difficulty spreading his or her legs. In another aspect, the system 10 can include a stand-alone urinal kit 34, without a collection bag. In another aspect, the system 10 can include a replacement bag kit 36. The system 10 can comprise at least two different types of the plurality of kits 14. Thus, the system 10 can provide an appropriate kit 14 with an appropriate urinal for the appropriate user and/or situation, as opposed to a one-size-fits-all approach that can lead to difficulties in use, and health and safety issues. For example, using an inappropriate urinal, such as a urinal that is too small or too large, or for a different gender, can lead to a urinary accident, and thus embarrassment, and even undesired ambulation of the user, and thus potential falls and injury. Referring to FIGS. 1 and 12, many of the kits 14 can comprise a urinal 50, a collection bag 38, a tube 42 interconnecting the urinal 50 and the collection bag 38, and instructions for use 44 contained in a package or bag 46, as described in greater detail below.

As indicated above, most of the kits 14 and the urinal systems 10 can contain a urinal 50, and each urinal can be adapted for use by a particular gender, size, and/or use or condition. By way of example, a urinal 50 for an adult male will be initially described, with other urinals being subsequently described, but all having some common features as apparent from the figures and description.

Referring to FIGS. 1-4, the urinal 50 can comprises a vessel 54 with a substantially flat bottom 58. In addition, the vessel 54 has an inclined neck 62 at a proximal end with an inlet 66 in the inclined neck 62 at the proximal end. Thus, the inlet 66 can form the proximal most end of the vessel 54. Furthermore, the vessel 54 has a nipple 70 extending from a distal end, opposite the proximal end, and an outlet 74 at the distal end, opposite the inlet 66. The inlet 66 can be elevated with respect to the outlet 74, and the outlet 74 can be substantially flush with an interior bottom of the vessel 54. A body of the vessel 54, intermediate the inlet 66 and the outlet 74, can be enlarged and can form a collection basin to receive and temporarily hold urine. During use, the urinal 50 and the vessel 54 can be positioned between a user's legs to receive urine through the inlet 66 and into the vessel 54. The inlet 66 can be sized and shaped to receive the user's genitals through the inlet 66, and into to the inlet 66, and in some instances into the neck 62. In one aspect, the urinal 50 and the vessel 54 can be formed of plastic and can be formed by rotational molding.

The urinal 50 can also have a handle 78 with a connection end affixed to the inclined neck 62 adjacent the inlet 66 and extending to a free end with a grip portion 82 of the handle 78 disposed over the vessel 54. The handle 78 and grip portion 82 allow the user to manipulate the urinal 50 and the vessel 54 into position and hold the urinal 50 during use. In one aspect, the handle 78 can be formed along with the vessel 54 as a single, unitary piece.

In addition, the urinal 50 can have a flexible ring 86 substantially circumscribing a perimeter of the inlet 66. In one aspect, the flexible ring 86 entirely circumscribes the perimeter of the inlet 66. The flexible ring 86 provides a cushion and an interface for contacting the skin without scratching. In addition, the flexible ring 86 can provide a seal against the user's skin. In one aspect, the flexible ring 86 can be formed of closed cell foam. The closed cell foam can resist absorbing urine. In another aspect, a smooth annular bead 88 (FIG. 2) of adhesive can be positioned between the flexible ring 86 and the neck 62 of the urinal 50 to provide a smooth interface with the user's skin and resist catching on skin, clothing and/or bedding. The smooth annular bead 88 can be formed inside and/or outside the neck 62 of the urinal 50. In one aspect, the adhesive can form a seal between the neck 62 and the flexible ring 86 to resist leakage of urine and/or smell. By way of example, the adhesive can be a flexible, waterproof adhesive, such as E-6100 available from Eclectic Products, Inc., of North Eugene, Oregon. In one aspect, an annular cylindrical slit can be formed in the flexible ring 86 to receive the neck 62. In another aspect, the slit can be formed by a cylindrical cutting bit.

Referring to FIGS. 1 and 2, the urinal 50 can also have a removable, protective cover 90. The removable cover 90 can be disposed on the inlet 66 of the urinal 50. The cover 90 can close the inlet 66 to resist inadvertent entry into the vessel 54 by items, such as dust, insects, etc., and/or to resist undesired exit from the vessel 54, such as odors, etc. The cover 90 can comprise a front 94 positioned over the inlet 66 and against a front of the flexible ring 86, and a perimeter wall 98 extending around the front 94 and receiving the inlet 66 and the ring 86 therein, and against a perimeter of the flexible ring 86. In one aspect, the cover 90, or the perimeter wall 98 thereof, can form a compression fit or an interference or friction fit with the perimeter of the flexible ring 86. Thus, the compression fit can form a seal to resist the escape of odor, etc. The cover 90 can also have an aperture 102 in the perimeter wall 98 to receive the handle 78 therethrough, and a slit 106 in the perimeter wall 98 from the aperture 102 to an end of the perimeter wall 98 to allow removal of the cover 90. Thus, the cover 90 can be selectively retained or completely removed and discarded. In one aspect, the cover 90 can be transparent so that the interior of the vessel 54 can be viewed. The cover 90 can be formed of plastic.

Referring to FIGS. 1-3, most of the kits 14 and the urinal systems 10 can contain a tube 42 coupled to and between the urinal 50 and the collection bag 38 to convey urine from the urinal 50 to the collection bag 38. Thus, the urinal 50 and the collection bag 38 can be located remote and spaced-apart from one another. In addition, the urinal 50 and the collection bag 38 can be located at different elevations, with the urinal 50 above the collection bag 38. For example, the urinal 50 can be located at the same level as a bed or seat, while the collection bag 38 can be suspended below the bed or seat. In addition, the collection bag 38 can be discretely positioned and concealed in a privacy satchel. The tube 42 can have a proximal end 110 coupled to the nipple 70 of the urinal 50 and the vessel 54, and an opposite distal end. In one aspect, the proximal end 110 of the tube 42 can be coupled to the nipple 70 with a press fit or interference fit, and/or adhesive. In another aspect, the nipple 70 can have an array of radial teeth 112 with the proximal end 110 of the tube 42 inserted by force over the teeth 112. In one aspect, the radial teeth 112 can have a saw-tooth profile. In another aspect, the radial teeth 112 can be ribs with a square-wave profile. In another aspect, the proximal end 110 of the tube 42 can include an adaptor or a connector with the proximal end 110 of the tube inserted in one end thereof, and the nipple 70 inserted in the other end thereof. The proximal end 110 of the tube 42 can be adhered in the one end of the connector, forming the proximal end 110 of the tube 42, while the other end of the connector is inserted over the nipple 70 and the teeth 112 as described above. Thus, the interior diameter of the tube 42 can be substantially flush with the interior diameter of the nipple 70 to resist undesired pooling or trapping of urine.

In addition, the tube 42 can have an intermediate coupler 118 located adjacent the nipple 70, and thus adjacent to the urinal 50 and the vessel 54. The intermediate coupler 118 can bifurcate the tube 42 into separable proximal and distal portions 122 and 124, respectively. Providing the intermediate coupler 118 allows for the urinal system 10 to be separable into two units or modules, namely: 1) the urinal 50, and 2) the collection bag 38 with the tube 42, or a majority thereof. Thus, while the urinal system 10 can be repeatedly used, or is reusable, the urinal 50 may outlast the collection bag 38 and/or tube 42. Thus, the existing collection bag 38 with the existing distal tubing portion 124 can be removed from the urinal 50 at the intermediate coupler 118, and replaced with a replacement collection bag 38 with a replacement distal tubing portion 124 with a replacement tubing coupler. In one aspect, the intermediate coupler 118 can comprise a quick-connection with a pair of quick-connect and quick-release tubing connections or couplers 126 and 128. In one aspect, the intermediate coupler 118 can include a finger-tight threaded connection. One connection 126 can be a female connection with internal threads, while the other connection 128 can be a male connection with external threads. The female connection can include a tube projection into the male connection. Each of the female and male connections can include an opposite barb to receive the tube 42, and the respective proximal and distal portions 122 and 124, in a secure manner.

In one aspect, the proximal portion 122 of the tube 42 coupled between the nipple 70 and the intermediate coupler 118 can have a shorter length and a greater stiffness than the distal portion 124 of the tube 42 coupled between the intermediate coupler 118 and the collection bag 38 which has a longer length and a lesser stiffness than the proximal portion 122. Thus, a great majority of the tubing 42, namely the distal portion 124, can remain flexible for ease of placement of the collection bag 38, while the proximal portion 122 can be stiff to resist kinking at the urinal 50. In one aspect, a length of the proximal portion 122 of the tube 42 between the nipple 70 and the intermediate coupler 118 is less than 2 inches. In another aspect, a length of the distal portion 124 of the tube 42 between intermediate coupled 118 and the collection bag 38 is greater than 36 inches. Even though the proximal portion 122 of the tube 42 can be stiffer than the distal portion 124, the proximal and distal portions 122 and 124 can have substantially the same outer diameter and substantially the same inner diameter to fit the barbs of the intermediate coupler 118 and the nipple 70.

In another aspect, the tube 42, and the proximal portion 122 thereof, can be or can include non-kink tubing to resist abrupt bending that would close the tubing and resist flow of urine. In one aspect, the tube 42 can include a plurality of internal, longitudinal ribs extending the length of the tubing. The ribs can have the same length as the tube 42 and can be arrayed circumferentially around the inner diameter of the tube 42. The ribs can make the tube 42 more ridged and more difficult to bend and kink.

Figures 5, 6:
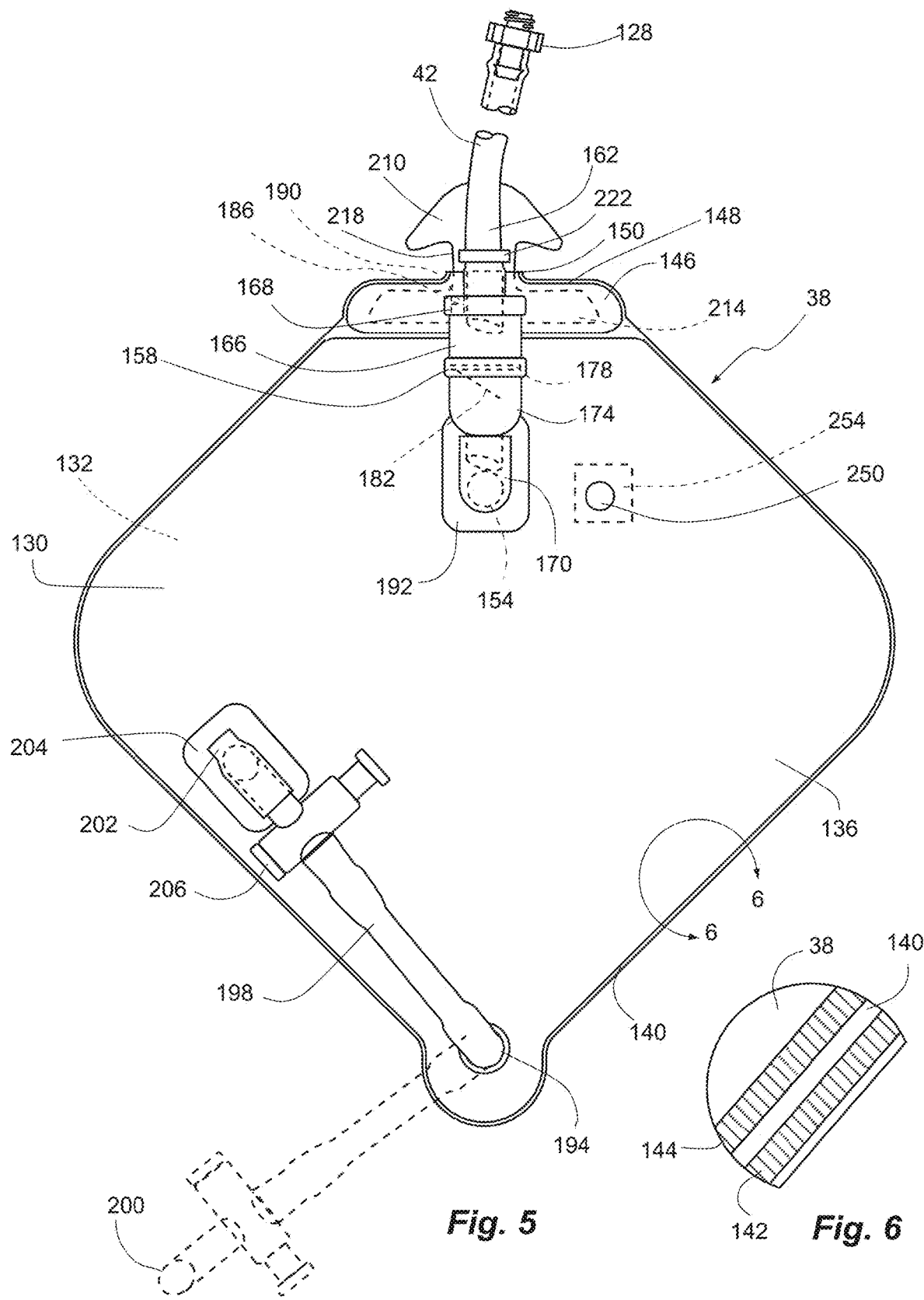
FIG. 5 is a front view of a collection bag of the urine collection and storage system of FIG. 1, showing a release tube in a stowed position in solid lines, and a release position in dashed lines.
FIG. 6 is a partial detail view of the collection bag of FIG. 5, showing a double seal.
Figure 7:
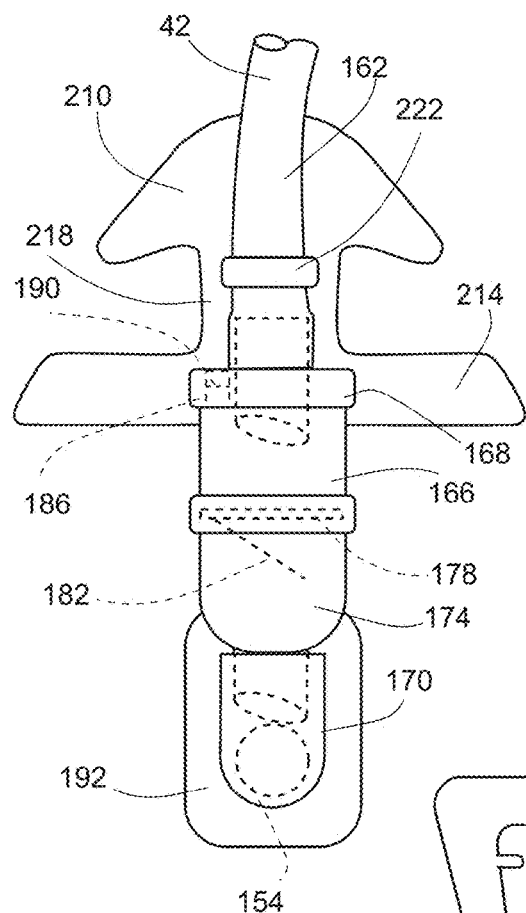
FIG. 7 is a partial front view a hanger and an anti-reflux valve of the collection bag of FIG. 5.

Referring to FIGS. 1, 5 and 6, most of the kits 14 and the urinal systems 10 can contain the collection bag 38 to receive urine from the tube 42 and to temporarily store the urine therein. In one aspect, the collection bag 38 can be the same for each kit and urinal system. Thus, the part count of the system 10 is reduced. In addition, as discussed above, the collection bag 38 can be affixed to the tube 42 to form a second part of the urinal system, in addition to the urinal 50, which can be separated from the urinal 50 at the intermediate coupler 118. Thus, an existing collection bag 38 with an associated existing tube 42 and distal tubing portion 124 and quick-connect and quick-release tubing connection 128 can be removed from the urinal 50, and replaced by a replacement collection bag 38 with a replacement tube 42 and distal tubing portion 124 and quick-connect and quick-release tubing connection 128, such as from the replacement bag kit 36.

The collection bag 38 is designed and constructed to be robust for prolonged use, and to resist leaks and spills, and to reduce odor. The collection bag 38 can comprise a pair of layers 130 and 132 joined together about substantially a perimeter to form a lower urine enclosure 136. As described above, leakage of the collection bag has been a disadvantage of prior devices.

Another disadvantage is that prior collection bags expand, leading to inaccurate fluid measurements. In one aspect, each of the layers 130 and 132 can have a thickness of at least 28 mil (0.028 in or 0.711 mm). In addition, the layers 130 and 132 are joined around substantially the entire enclosure 136 with a double seal or weld 140. Thus, substantially the entire enclosure 136 is surrounded with two separate and distinct welds 140 that can be spaced-apart and parallel with respect to one another. The double seal 140 includes an outer seal 142 adjacent the perimeter along substantially an entire length of the perimeter and an inner seal 144 spaced-apart from the outer seal 142. The double seal or weld 140 can be formed by sonic welding.

In another aspect, at least one of the layers 130 can be at least light translucent so that the level of urine in the enclosure 136 can be viewed through the layer. A graduated scale can be printed on the layer 130 that is indicative of the volume of urine in the enclosure 136. In addition to the lower urine enclosure 136, the pair of layers 130 and 132 can also be joined together to form an upper hanger pocket 146, separate from the lower urine enclosure 136. The hanger pocket 146 can have a substantially horizontal top wall 148 and a hanger opening 150 therein.

Referring to FIGS. 5-9, the collection bag 38 also has an upper inlet 154 in one of the layers 130 that is position adjacent an upper end of the collection bag 38. An anti-reflux chamber 158 can be coupled to the collection bag 38, or the layer 130 thereof, and the tube 42. The anti-reflux chamber 158 has an upper inlet coupled to the distal end 162 of the tube 42, and a lower outlet coupled to the upper inlet 154 of the collection bag 38. Thus, the anti-reflux chamber 158 is disposed between the distal end 162 of the tube 42 and the upper inlet 154 of the collection bag 38.

The anti-reflux chamber 158 comprises an upper chamber 166 with a top plate 168 coupled to the distal end 162 of the tube 42. In addition, the anti-reflux chamber 158 has a lower chamber 170 coupled to the upper inlet 154 of the collection bag 38. An intermediate chamber 174 is positioned between the upper and lower chambers 166 and 170. The intermediate chamber 174 has a vertical outlet into the lower chamber 170 such that the vertical outlet is offset with respect to the collection bag 38. An annular flange 178 is positioned between the upper and intermediate chambers 166 and 174. A flap 182 is pivotally coupled to a bottom of the annular flange 178 and forms a check valve to only allow flow in one direction. The flap 182 is normally closed and normally abuts to the annular flange 178, but is shown in an open configuration for ease of viewing. Thus, the flap 182 normally abuts the bottom of the annular flange 178 and is biased in a closed position. The flap 182 resists the flow of urine and/or the smell of urine out of the collection bag 38 and back through the tube 42. In one aspect, a vent hole 186 is in the top plate 168 and covered by a liquid-impermeable but air-permeable membrane 190. Thus, the anti-reflux chamber 158 and the tube 42 can vent without releasing urine. A flange 192 of the lower chamber 170 can be affixed to one of the layers 130 of the collection bag 38, such as by adhesive or sonic welding.

The collection bag 38 also has a lower outlet 194 in one of the layers 130 adjacent a lower end of the collection bag 38. A flexible release tube 198 is coupled to the lower outlet 194 of the collection bag 38, and has a free open end 200. The flexible release tube 198 is used to drain urine from the collection bag 38. Thus, the collection bag 38 can collect urine over time, such as through the night, and then can be drained at a more convenient time, such as in the morning. In addition, the intermediate coupler 118 allows the collection bag 38 to be separated from the urinal 50 for draining and transport to a draining location. A downward facing pocket 202 can be carried by one of the layers 130 to receive and selectively retain the free open end 200 of release tube 198. Retaining the free end 200 of the tube 198 in the pocket 202 can resist the escape of odor. In addition, facing the pocket 202 downward resists the accumulation of urine, and thus the odor.

The flexibility of the tube 198 allows it to bend and flex to be removed from and inserted into the pocket 202. The release tube 198 has a stowed position, as shown in solid lines in FIG. 5, in which the free end 200 of the tube 198 is located in the pocket 202, and a release position, as shown in phantom lines in FIG. 5, in which the free end 200 of the tube 198 is out of the pocket 202 and the tube 198 can be directed downwardly to drain. The pocket 202 can have a flange 204 affixed to one of the layers 130 of the collection bag 38, such as by adhesion or sonic welding. The pocket 202 can be positioned adjacent a lateral side of the collection bag 38, so that the release tube 198 is positioned to the lateral side when stored. Positioning the release tube 198 to the side aids in viewing the contents of the collection bag 38 and the scale. A drain valve 206 is carried by the release tube 198 and has an open position (shown in phantom lines in FIG. 5) and a closed position (shown in solid lines in FIG. 5) to allow the urine to be selectively drained. The drain valve 206 can be positioned in-line with the tube 198 to resist movement and lose of the valve. In addition, the drain valve 206 can hold the open and closed positions to resist fumbling with the valve.

Referring to FIGS. 5-9, the collection bag 38 also has a hanger 210 coupled thereto and adapted to suspend the collection bag 38 pendant therefrom. Thus, the hanger 210 can be used to suspend the collection bag 38 from a chair or bed adjacent the urinal 50. The hanger 210 can comprise a tab 214 with a horizontal top disposed in the upper hanger pocket 146 of the collection bag 38, and a neck 218 extending from the tab 214 and through the hanger opening 150. The tab 214 has a width greater than the hanger opening 150 in the collection bag 38 so that the horizontal top wall 148 of the hanger pocket 146 hangs on the tab 214. The hanger 210 also has a front loop 222 receiving the tube 42 therethrough to resist the tube 42 pulling on the collection bag 38 or the layer 130 thereof.

Figure 8:
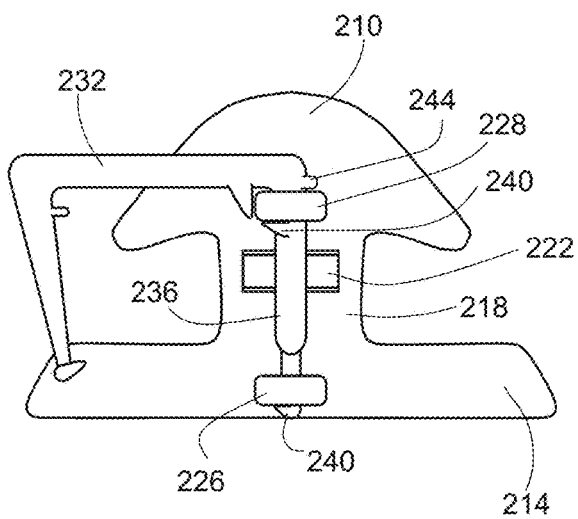
FIG. 8 is a rear view of the hanger of the collection bag of FIG. 5.
Figure 9:
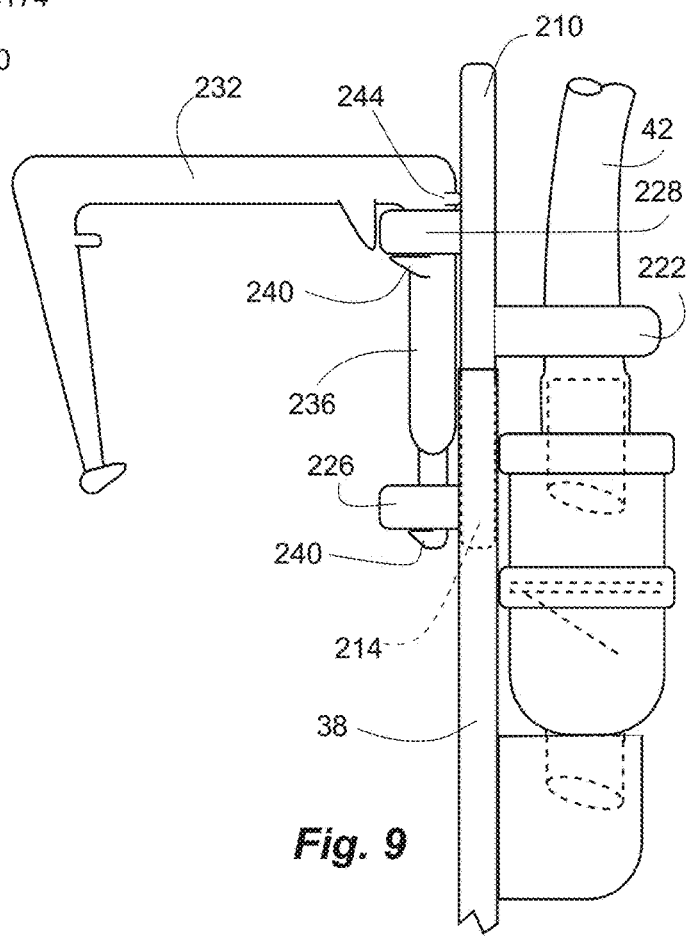
FIG. 9 is a partial side view of the hanger and the anti-reflux valve of the collection bag of FIG. 5.

The hanger 210 also has a pair of spaced-apart rear loops 226 and 228 extend from a back of the hanger 210. A lower loop 226 can extending through one of the layers 132 of the collection bag 38 to further support the collection bag 38. A hook 232 can be pivotally coupled to the hanger 210. The hook 232 can have an inverted U-shape. The hook 232 can have a vertical column 236 pivotally received in the pair of spaced-apart loops 226 and 228. The hook 232 can pivot between a stored orientation adjacent the collection bag 38 and the hanger 210, as shown in FIG. 8, and a use orientation extending outward from the collection bag 38 and the hanger 210, as shown in FIG. 9. The vertical column 236 can have inclined enlargements 240 adjacent the loops 226 and 228 that allow the inclined portion of the enlargement 240 to be pressed through the respective loop 226 and 228, and an abutment surface that resists removal of the enlargement 240 from the loops 226 or 228. The hook 232 or the vertical column 236 thereof can have a tab 244 extending therefrom towards the hanger 210 and bearing against the hanger 210 to resist pivotal movement of the hook 232 between the two orientations. Thus, the hook 232 tends to stay in an orientation unless deliberately pivoted sufficient to force the tab 244 past the hanger 210.

Furthermore, the collection bag 38 can have a vent hole 250 in one of the layers 130 adjacent the upper end of the collection bag 38 and covered by a liquid-impermeable but air-permeable membrane 254. Thus, the bag 38 can be vented.

As stated above, the system 10 and each of the kits 14 can have a urinal adapted for use by a particular gender, size, and/or use or condition. The adult male system or kit 18 (FIG. 1) can have a urinal 50 with an enlarged inlet 66 (enlarged with respect to a reduced inlet of the urinal of the juvenile system or kit) with a substantially flat, circular opening oriented at an incline between approximately 35-55 degrees in profile, as shown in FIGS. 1 and 2. The urinal 50 can comprise a neutral color, such as white. For example, the flexible ring 86 can be white. It is believed that a neutral color, such as white reduces the stigma associated with use. Various aspects of the urinal 50 described above are equally applicable to the following urinals.

Referring to FIGS. 10-12, the adult female system or kit 20 (FIG. 12) can have a urinal 50b with an enlarged inlet 66b (enlarged with respect to a reduced inlet of the urinal of the juvenile system or kit) with a concave profile. The juvenile male system or kit 22 (FIG. 12) can have a urinal 50c with a reduced inlet 66c (compared to the enlarged inlet 66 of the adult male urinal 50) with a substantially flat, circular opening oriented at an incline between approximately 35-55 degrees in profile. In addition, the urinal 50c can comprise the color blue, such as with a flexible ring 86c that is blue. It is believed that the color will provide comfort to juvenile users and encourage use. The juvenile female system or kit 26 (FIG. 12) can have a urinal 50d for the juvenile female system with a reduced inlet 66d (compared to the enlarged inlet 66b of the adult female urinal 50b) and with a concave profile. In addition, the urinal 50d can comprise the color pink, such as with a flexible ring 86d that is pink. It is believed that the color will provide comfort to juvenile users and encourage use.

The close-fit system or kit 30 (FIG. 12) for a retracted male can have a urinal 50e with an enlarged inlet 66e (with respect to the reduced inlet 66c or 66d of the urinal of the juvenile urinals 50c and 50d) with a concave profile. The enlarged inlet 66e and the concave profile can provide a closer fit for a retracted male. The urinal 50e can comprise a neutral color, such as grey. For example, the flexible ring 86e can be grey. Thus, although the inlet 66e for the retracted male is shaped as the inlet 66b for the female urinal 50b, the color is different to distinguish it from the female urinal. It is believed that a neutral color, such as grey reduces the stigma associated with use.

The slim-fit system or kit 32 (FIG. 12) can have a urinal 50f with a narrower inlet 66f (compared the enlarged inlets 66 or 66b of the adult urinals 50 and 50b). In addition, the urinal 50f can have a narrower vessel 54f than the vessels 54 of adult male and adult female urinals 50 and 50b. The narrower inlet 66f and the narrower vessel 54f can be easier to use by individuals with difficulty spreading his or her legs. The urinal 50f can have a more neutral color, such as white.

The stand-alone system or kit 34 (FIG. 12) can have a stand-alone urinal 50g without a collection bag. The urinal 50g can have an inlet 66g similar to any of those described herein, but a closed distal end 76 opposite the inlet 66g. The distal end 76 can be broad and flat, and can form a base for the urinal 50g to stand upright. Thus, the urinal 50g can have a use orientation resting on a flat bottom 58 between the inlet 66g and the distal end 76, and a storage orientation resting on the flat distal end 76. Thus, the stand-alone system 34 and the stand-alone urinal 50g can be utilized by someone who is more ambulatory and does not require the collection bag 38. In addition, the stand-alone urinal 50g can have a flexible ring 86 and a cover 90 as described above.

As described above, the replacement bag kit 36 can comprise a replacement collection bag 38, a tube 42, and a quick-connect and quick-release tubing connection 128. The replacement collection bag 38 can be used with any of the systems or kits described above, except for the stand-alone kit and urinal.

In another aspect, some of the urinals have can inlets and flexible rings that are shaped to contact the skin around the genitals. Thus, some of the urinals can have a vent hole in the vessel adjacent to the handle to counteract a seal that may form between the skin and the inlet and ring, and thus facilitate drainage of urine out of the vessel through the outlet. For example, the adult female urinal 50b, the juvenile female urinal 50d, and the close-file retracted male urinal 50e, can have a vent hole 256 in a top of the vessel 50b, 50d, and 50e, respectively, or neck 62, and adjacent the handle 78 or its connection end affixed to the neck 62 or vessel. In one aspect, the vent hole 256 can be formed in the neck 62, and immediately adjacent to or under the connection end of the handle 78.

The urine collection and storage system 10 can provide a plurality of different reusable urine collection and storage kits 14, each with a urinal 50, 50b, 50c, 50d, 50e and/or 50f adapted to a user's gender, age and/or condition.

Each of the kits 14 can comprise one of the urinals 50, 50b, 50c, 50d, 50e or 50f, the collection bag 38, the tube 42, and the instructions 44 for use contained in the package or bag 46. In addition, the system 10 can comprise a stand-alone system or kit 34 with a stand-alone urinal 50g. Furthermore, the system 10 can further comprise a replacement bag kit 36 comprising a collection bag 38 and a distal portion 124 of a tube 42 coupled to the collection bag, along with instructions 44 disposed in a package or bag 46. Thus, an existing, used collection bag 38 and tube 42 (or distal end thereof) can be separated from an existing urinal 50 (and proximal end 122 of the tube 42) at the intermediate coupler 118, and a new collection bag 38 and tube 42 (or distal end 124 thereof) can be coupled to the existing urinal 50 (and proximal end 122 of the tube 42) at the intermediate coupler 118. Thus, the urinal 50 can be used for longer than the collection bag 38, but the useful life of the urinal 50 can be extended by using a replacement collection bag 38. Thus, an appropriate urinal adapted to a user's gender, age and/or condition can be provided. The system addresses a user's anatomy and emotional condition associated with their ambulatory condition. In addition, the system allows the user to remain immobile to avoid falls associated with ambulation to the bathroom. Furthermore, the system addresses issues with respect to odor by keeping the system closed and avoiding spills.

Various aspects of urinals are shown in U.S. Pat. Nos. 6,070,275; D399,308; D497,981, which are hereby incorporated herein by reference. Referring to FIGS. 13-18, the urinal system can be a modular urinal system 310. The modular urinal system 310 can include a urinal 350 and a vessel 354 similar to those described above, but which can be couple to one of a plurality of modular receivers 340a-e. The modular receivers 340a-e can be adapted to a user's gender, age and/or condition, as described above.

For example, an adult male receiver 340d (FIG. 14e), similar to the adult male urinal 50 above, can have a large planar opening better suited for a large adult male user. Similarly, an adolescent or juvenile female receiver 340c (FIG. 14c), similar to the juvenile female urinal 50d above, can have a smaller opening and a concave cupped profile better suited for a smaller juvenile female user. As such, each user can choose a modular receiver that is more comfortable for their personal characteristics so as to make the modular urinal system 310 customizable to meet any particular user's needs. Thus, the system 310 can include a plurality of different receivers, some having different sized planar openings designed for different sized males, and some with concave cupped profiles having different shaped and sized cupped profiles with protruding lips designed for different sized and shaped females.

Female specific modular receivers 340a-c are shown in FIGS. 14a-c. A larger adult female receiver 340a (FIG. 14a), similar to the adult female urinal 50b above, can have a concave profile and a protruding lip can be suited for use by an adult female. A medium female urinal 340b (FIG. 14b) can have a smaller concave profile and a protruding lip. A smaller female urinal 340c (FIG. 14c), similar to the juvenile female urinal 50d above, can have a concave profile and a protruding lip that can be suited for use by a juvenile female. Each of the female receivers can have a padded area, such as the flexible ring 86 above, about the circumference of the inlet and protruding lip to provide additional comfort and conformation to the user's individual shape.

Male specific modular receivers 340d-e are shown in FIGS. 14d and e. An adult male receiver 340d (FIG. 14d), similar to the adult male urinal 50 above, can have a larger planar opening with a padded ring about the circumference of the receiver to provide additional comfort and a certain degree of conforming. A juvenile male receiver 340e (FIG. 14e), similar to the juvenile male urinal 50 above, can have a smaller planar opening with a padded ring about the circumference of the receiver to provide additional comfort and a certain degree of conforming.

Figure 13:
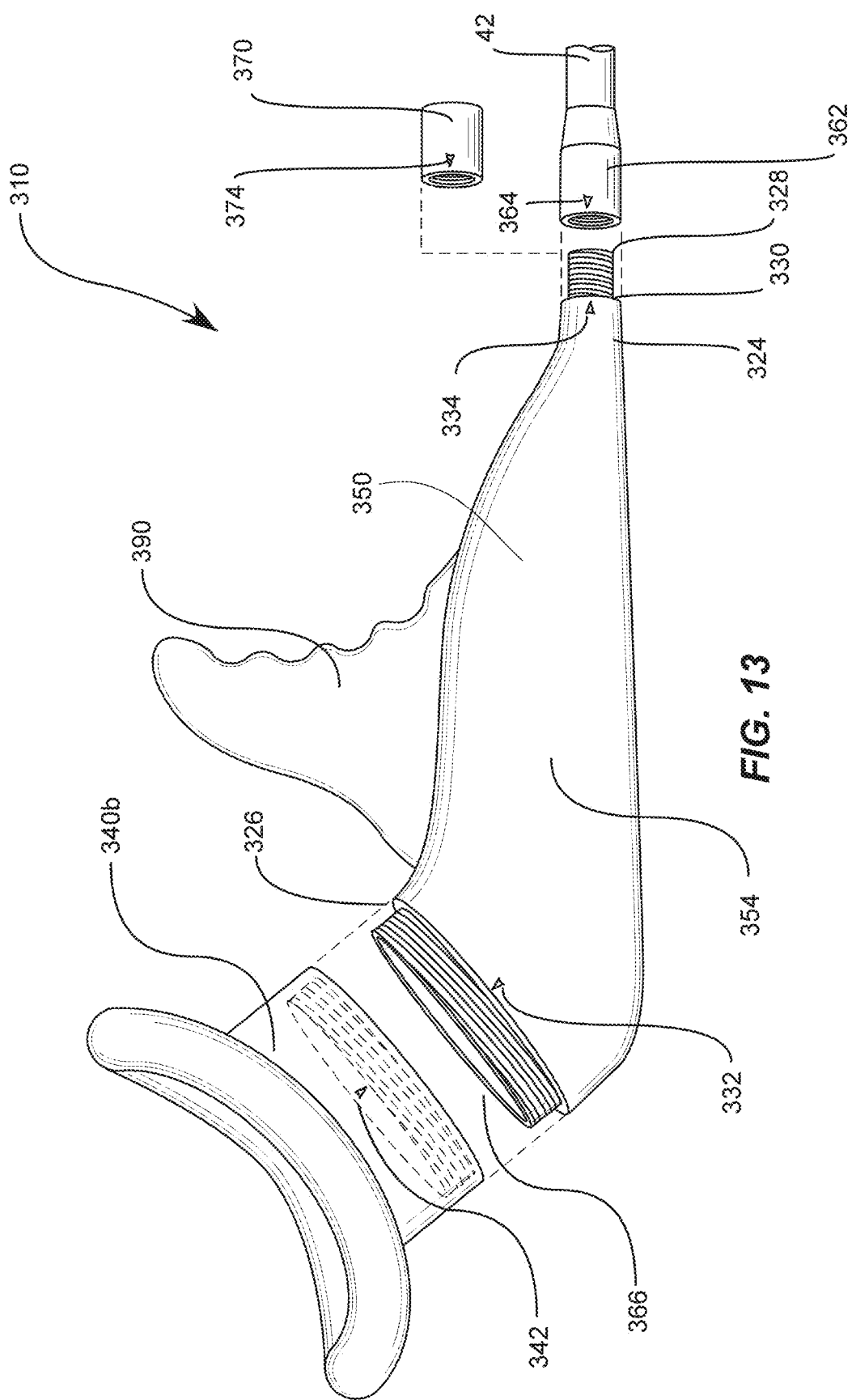
FIG. 13 is a partial side schematic view of another urinal in accordance with an example embodiment.
Figure 14:
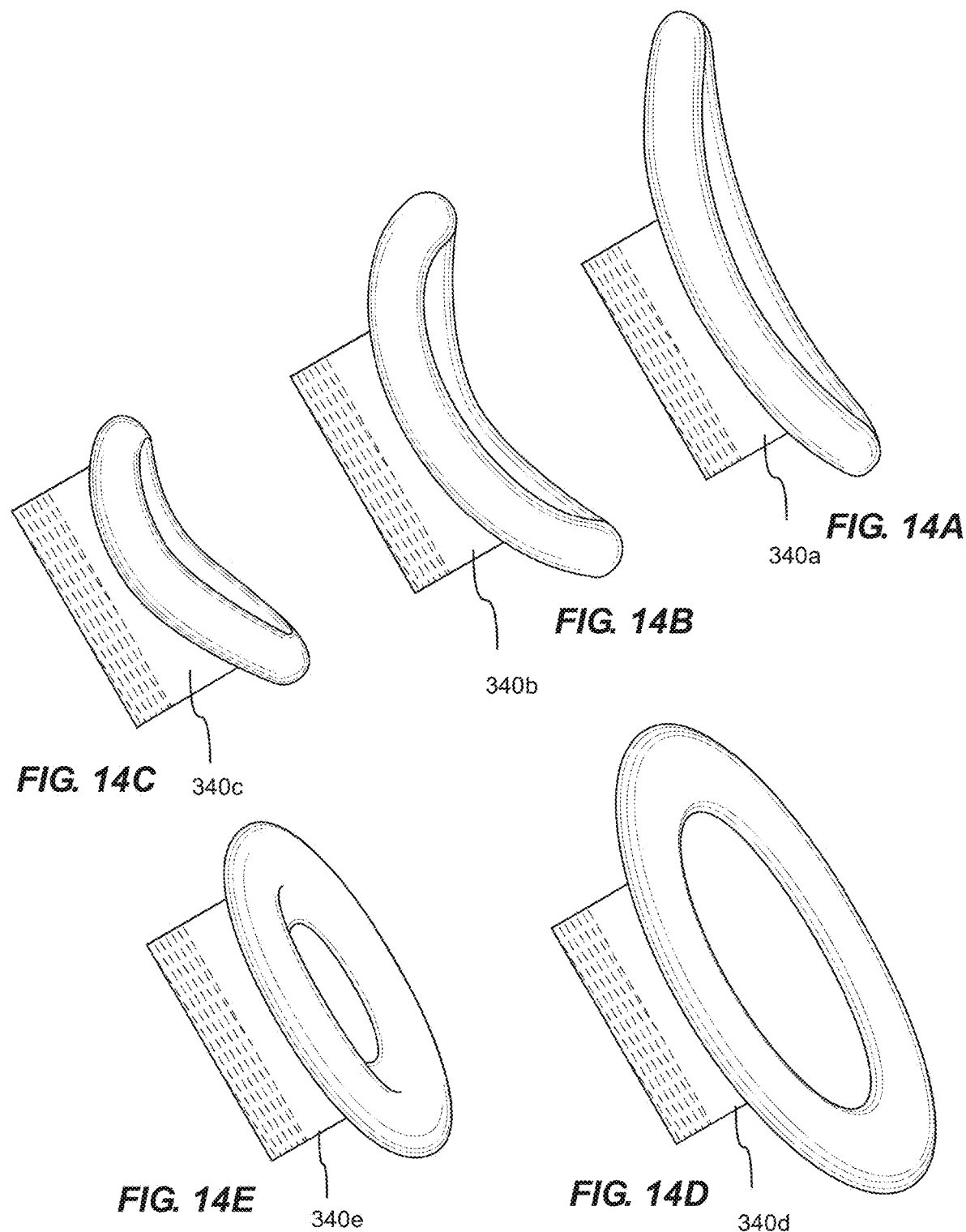
FIGS. 14a-e are side views of different receivers of the urinal of FIG. 13.

Referring to FIG. 13, the receiver (340b by way of example) and the vessel 354 can be coupled together at an inlet interface. The inlet interface provides a transition point where the outer surface of the vessel 354 and the receiver 340b match and are flush. If the outer surfaces of the vessel 354 and the receiver 340b do not match up properly, an exterior raised ridge can result. A sharp edge which can present several problems. For example, a raised edge presents the possibility of such an edge catching or otherwise snagging the clothing or bedding during and after use. Such snagging may jar the vessel and cause undesired spilling. Further, a raised edge may cut or otherwise injure the user or cause related discomfort when placed between the user's legs.

Therefore, in order to eliminate such a raised edge or protrusion, the vessel 354 can include an inlet shoulder 326. The inlet shoulder 326 can be a slight lip around a circumference of the inlet 366 of the vessel 354 such that the inlet shoulder 326 abuts against an outer rim or edge of the modular receiver 340b. In this way, an outer surface of the modular receiver 340b and an outer surface of the vessel 354 at the inlet shoulder 326 match up and have a common radius. Thus, when the modular receiver 340b is coupled to the vessel 354 at the inlet interface, the vessel 354 and the modular receiver 340b abut against one another, and the inlet interface is substantially flush and smooth. The substantially flush and smooth inlet interface between the modular receiver 340b and the vessel 354 reduces any sharp ridges or raised protrusions which can catch on the user's clothing or bedding, and perhaps cause the user to spill the contents of the vessel. Further, such a flush transition point and/or area eliminates sharp edges which can cut, injure, or otherwise cause discomfort to, the user when the urinal is placed between the user's legs for use.

The modular urinal system 310 can also provide at least two modes in which the system can operate in order to be more convenient for use based on particular scenarios in which the user may find themself. For example, during the day, a user can carry the modular urinal system 310 with them as they travel about. In such a scenario the modular urinal system 310 can be portable while still allowing for instantaneous access for use. After use, the vessel 354 can be easily transported to an appropriate location and emptied prior to a subsequent use. Therefore, a first single-use mode can be employed is such situations. In the single-use mode, a cap 370 can be coupled to an outlet 328 at a distal end 324 of the vessel 354, closing the outlet 328. In one aspect, the cap 370 and the distal end 324 can be threaded. In the single-use mode, the urinal 350 can be smaller, more portable, and easier to carry around with the tube 42 and the collection bag 38 coupled thereto.

During the night, a user can be in an immobile state, or can otherwise be unable to arise and go to the bathroom. In such a situation the vessel 354 of the modular urinal system 310 can be coupled to a collection bag 38 as described above. In the continuous-use mode, the tube 42 can be coupled to the outlet 328 at the distal end 324 of the vessel 354, opening the outlet 328. In the continuous-use mode, the urinal 350 and the vessel 354 can be used repeatedly with urine flowing through the tube 42 and into the collection bag 38, and without the need to transport the vessel 354 to an appropriate emptying place in between each use. The tube 42 can be removably coupleable to the outlet 328 of the vessel 354. The tube 42 can have a tube connector 362 to couple to the outlet 328. The tube connector 362 can be threaded.

In addition, similarly to the inlet interface, an outlet interface can occur at the transition point between vessel 354 and either the cap 370 or the tube connector 362. Further, for similar reasons as discussed above with respect to the inlet interface, the outlet interface can also be provided with substantially flush and smooth outer surfaces. The substantially smooth outlet interface can be achieved with an outer diameter of the outlet 328 of the vessel 354 being substantially the same as an outer diameter of the cap 370 and the tube connector 362. The outlet 328 and the vessel 354 can also have a shoulder 330 to resist any raised edge or protrusion at the outlet interface. The outlet shoulder 330 can include a slight lip around a circumference of the outlet 328 of the vessel 354 so that the outlet shoulder 330 abuts against an outer rim or edge of the cap 370 or the tube connector 362. Thus, the outer surface of the vessel 354 can be flush and smooth with the cap 370 or the tube connector 362; reducing the chances of the distal end 324 of the vessel 354 catching on something during or after use and potentially causing the user to spill the contents.

Figure 17:
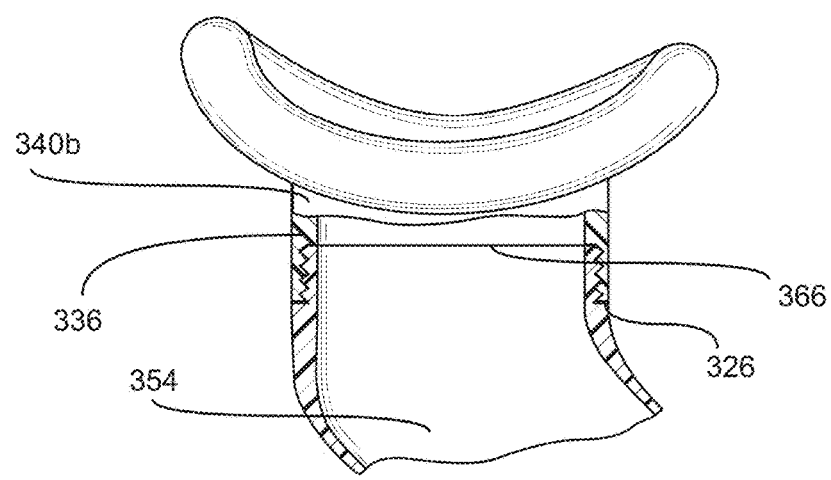
FIG. 17 is a partial cross-sectional side view of a receiver of the urinal of FIG. 13.
Figure 18:
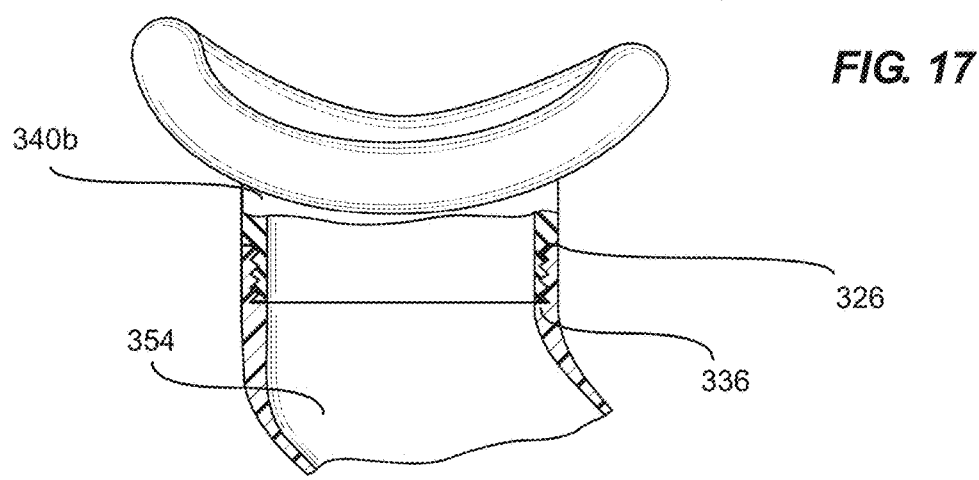
FIG. 18 is a partial cross-sectional side view of a receiver of the urinal of FIG. 13.

In addition, the vessel 354 can also have a smooth inner surface at the inlet interface. Referring to FIGS. 17 and 18, an interior shoulder 336 can be provided on the interior surface of the receiver 340b so that the outer edge of the inlet 366 of the vessel 354 can abut against this interior shoulder of the receiver 340b. When the interior shoulder 336 of the modular receiver 340b and the outer edge of the inlet 366 are abutting, the interior surface at the inlet interface can be flush and smooth. Such a flush and smooth transition of the interior surface between the receiver 340b and the vessel 354 to resist discomfort or pain during use. In addition, the flush and smooth transition can resist urine pooling or collection, and thus reduce unwanted odors.

Figure 19:
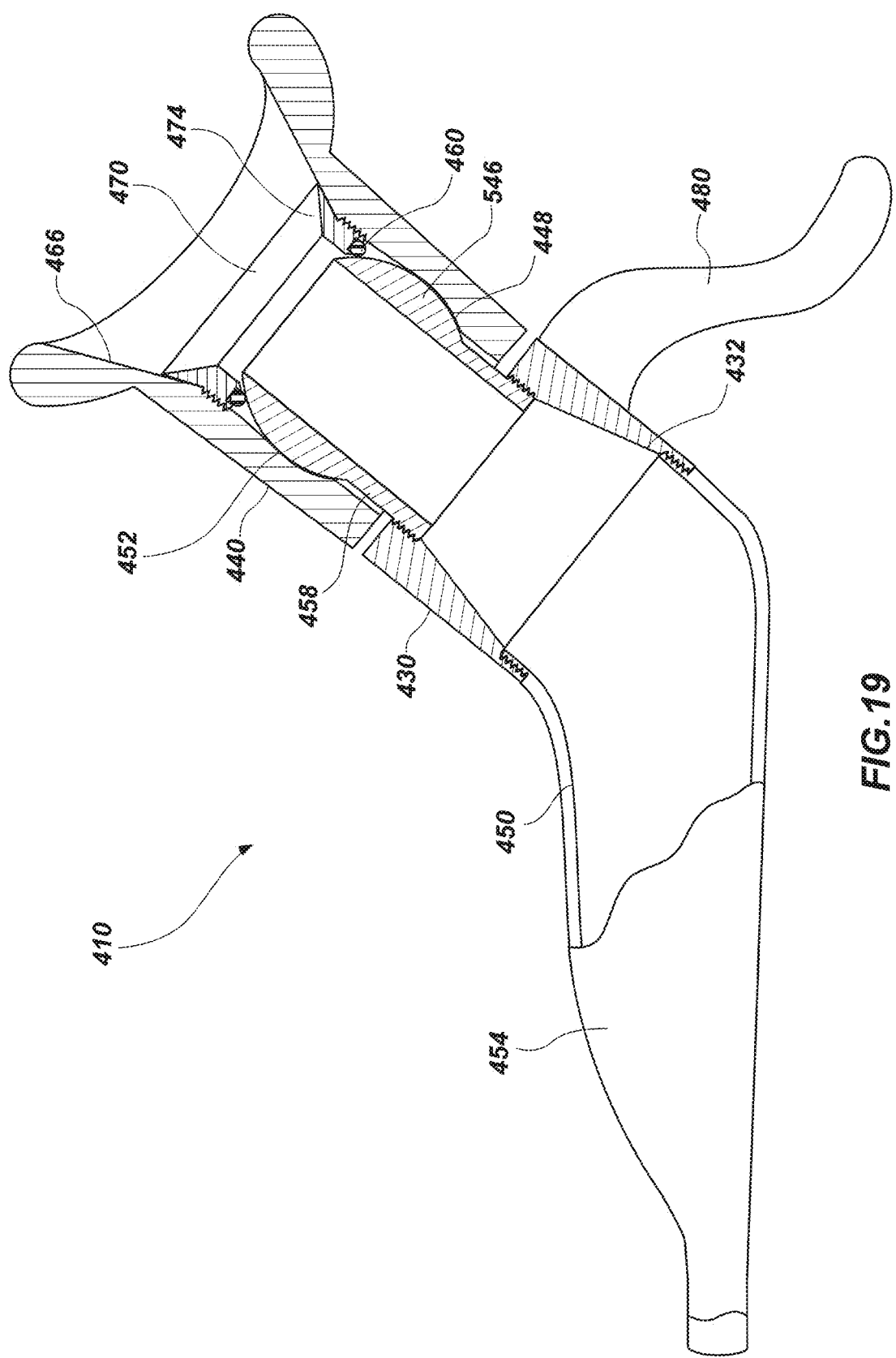
FIG. 19 is a partial cross-sectional side view of another urinal in accordance with an example embodiment.

Referring to FIG. 17, the urinal 350 and the vessel 354 are shown with threads on an exterior portion of the vessel 354, and corresponding threads an interior portion of the receiver 340b. Referring to FIG. 19, the urinal 350 and the vessel are shown with the threads on an outer portion of the receiver 340b, and corresponding threads on an interior surface of the inlet 366 of the vessel 354. In addition, the inlet shoulder 326 can be provided on the outer surface of the receiver 340b, and an interior shoulder 336 can be provided on the interior surface of the inlet of the vessel 354 so that both the outer and inner surfaces are substantially flush and smooth at their relative transition points.

Referring again to FIG. 13, the vessel 354 can have inlet indicia 332 and outlet indicia 334. The inlet indicia 332 can work in conjunction with modular receiver indicia 342 such that the indicia can indicate when the receiver 340b is fully installed. For example, if a threaded or other type of twist-lock coupling mechanism is used, the inlet indicia 332 can line up with the receiver indicia 342 to indicate to the user that the receiver 340b is fully installed or how to align the receiver 340b with the vessel 354 to engage the twist-lock.

Similarly, outlet indicia 334 can be provided at the outlet 328 of the vessel 354 and corresponding indicia 374 and 364 can be located about the cap 370 and the tube connector 362, respectively, to indicate that such are fully installed on the vessel 354. Such indicia can eliminate confusion regarding when a seal has been established between the various components, and thus reduce unwanted leaks.

Figure 16:
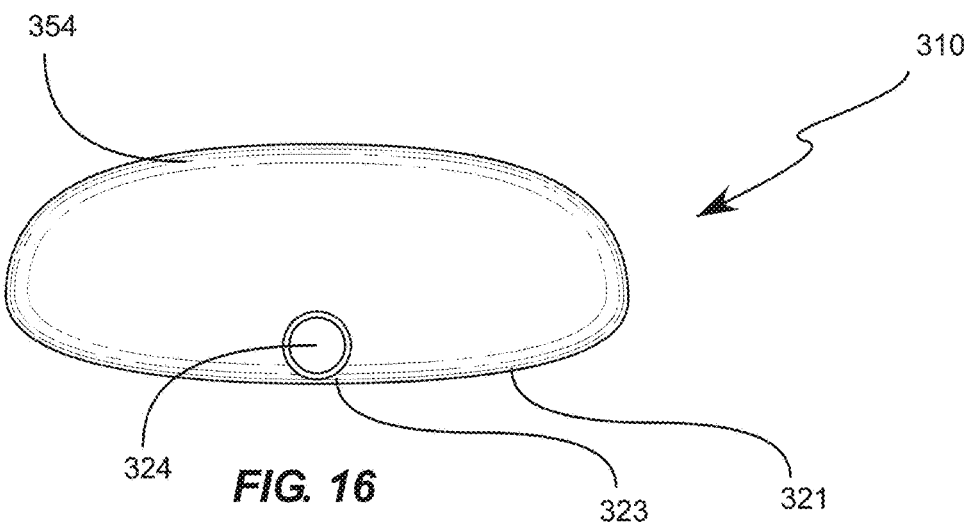
FIG. 16 is an end view of the urinal of FIG. 13.

Referring to FIG. 16, the bottom 321 of the vessel 354 can be tapered to a central channel 323 which terminates in the outlet 328 of the vessel 354. In this manner no recesses are present on the interior surface of the vessel 354 and any liquids within the vessel 354 will drain completely out of the vessel and will not pool within such recesses. Having a tapered bottom 321 which continuously drains ensures the contents will not result in undesirable odors, or intensive cleaning associated with the urine collecting and stagnating is such recesses.

Figure 15:
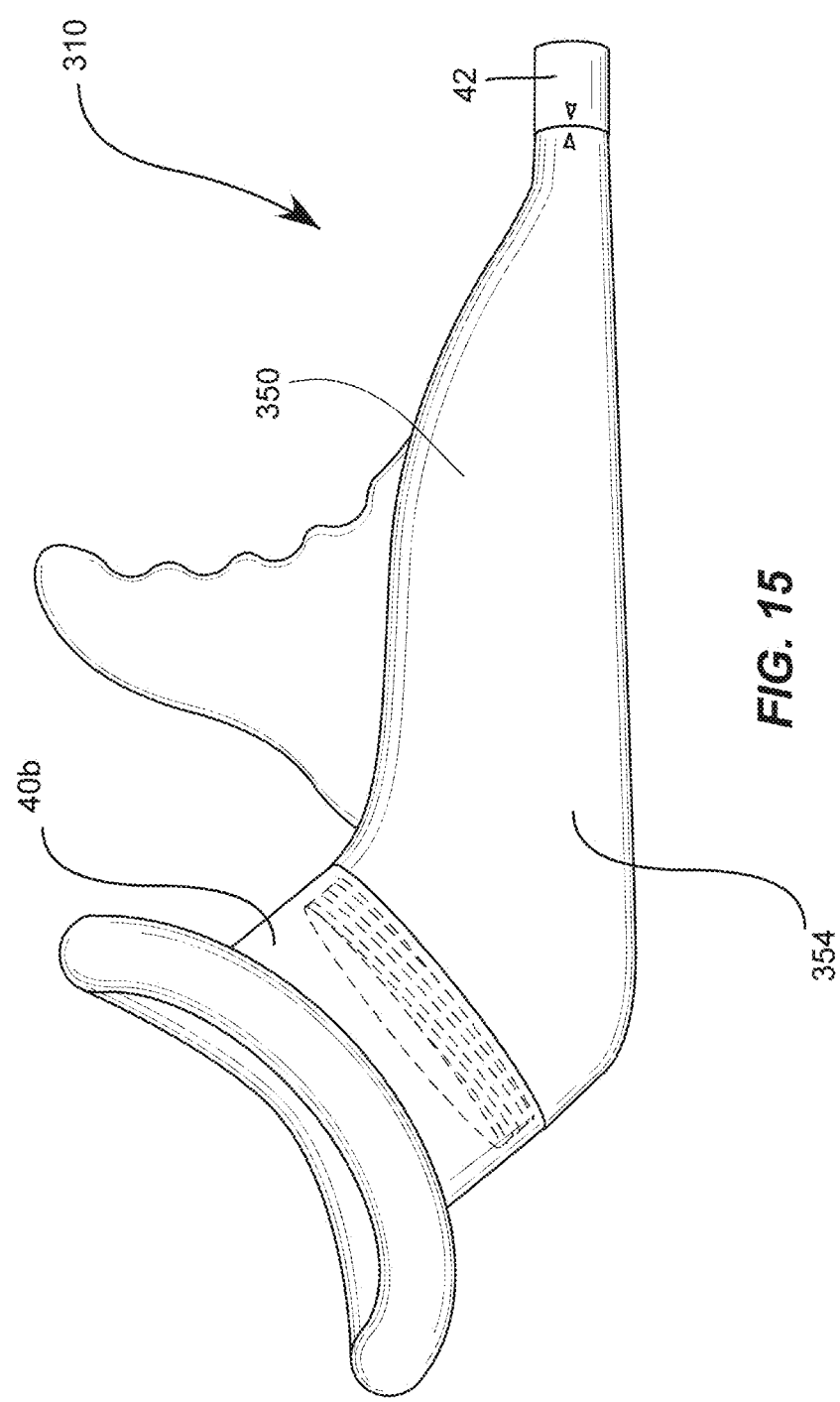
FIG. 15 is a side view of the urinal of FIG. 13.

Referring to FIGS. 13 and 15, the urinal 350 and the vessel 354 can be provided with a handle 390 that extends upwardly from the vessel 354 and that has a grip with finder indentations. The handle 390 can have a profile with a wider bottom and a narrower top. Thus, the handle 390 is shaped and positioned to facilitate handling.

In one aspect, a method of using the modular urinal system 310 can include selecting a receiver 340a-e to match the user's gender and size. Once an appropriate receiver is selected, such receiver 340a-e can then be coupled to the inlet 366 of the vessel 354. In one aspect, the tube 42 can be coupled to the outlet 324 of the vessel 354 for use in the continuous-use mode. In another aspect, the cap 370 can be coupled to the outlet 324 of the vessel 354 for use in the first single-use mode.

Figure 20:
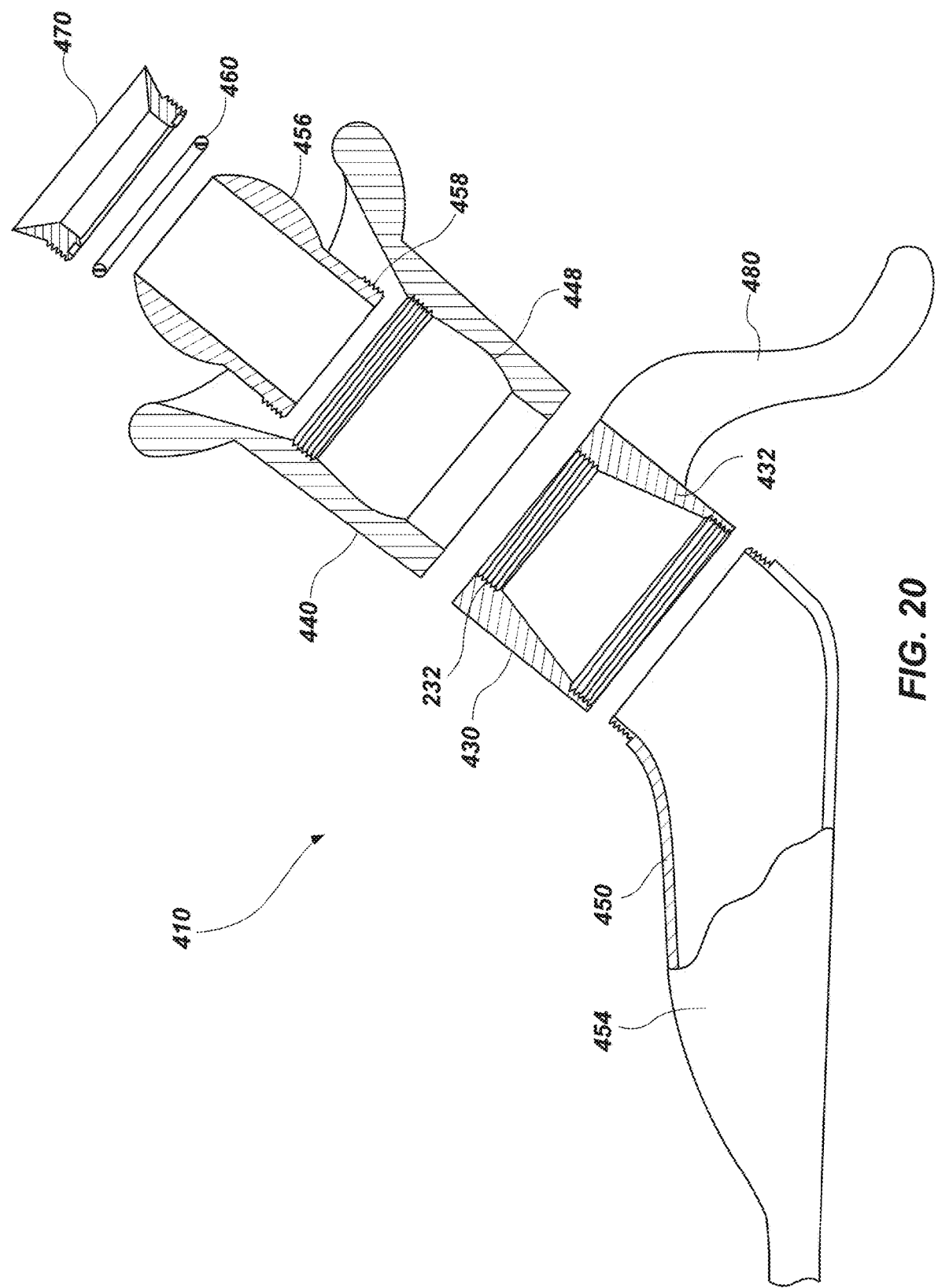
FIG. 20 is a partial cross-sectional exploded view of the urinal of FIG. 19.

Referring to FIGS. 19 and 20, the urinal system can be an adjustable urinal system 410 with an adjustable urinal 450. The adjustable urinal 450 has a pivotal inlet 466 and receiver 440 with an adjustable angle that can pivot up and down, and even side to side. In one aspect, the urinal 450 can have a ball-and-socket joint 452 positioned between the vessel 454 and the inlet 466 and the receiver 440. The receiver 440 can have a socket 448 with a semi-spherical shape therein. The vessel 454 can have a shaft 458 with a ball end 456. The ball end 456 can have a semi-spherical shape that corresponds in size and shape to the socket 448. In addition, the ball end 456 and the shaft 458 can have a bore therethrough. The socket 448 of the receiver 440 can receive the ball end 456 of the shaft 458. The receiver 440 and the inlet 466 can pivot about the ball end 456 of the shaft 458 and the vessel 454 to angle the inlet 466 with respect to the vessel 454 as desired. The ball end 456 and the socket 448 can create a seal between them when the ball end 456 is inserted into the socket 448. In addition, the ball end 456 and the socket 448 can have a friction fit therebetween to maintain the orientation of the receiver 440 and the inlet 466.

An o-ring or gasket 460 can be provided between an upper portion of the ball end 456 and the socket 448 to further protect against leakage and to resist fouling of the ball-and-socket joint 452. The gasket 460 can be held in place by a retaining nut 470 which can have exterior threads which correspond to interior threads of the socket 448 and receiver 440. The retaining nut 470 can have a flared opening 474 with a wider outer opening and a narrower inner opening to match a contour of the receiver 440 and the inlet 466. The flared opening 474 can have a taper so that the outer opening abuts to and is flush with the inner surface of the receiver 440. A resistance to movement between the ball end 456 and the socket 448 can be adjusted by adjusting the tightness or tension of the retaining nut 470. Tightening the retaining nut 470 can cause the friction between the ball end 456 and the socket 448 to increase, thus further resisting movement between, and even locking, the ball end 456 and the socket 448. Similarly, loosening the retaining nut 470 can allow for more free motion between the vessel 454 and the receiver 440 and the inlet 466.

The shaft 458 can also have a threaded end that passes through the receiver 440 and coupled to the vessel 454. The shaft 458 can have a length to space the receiver 440 from the vessel 454 to allow for angular positioning between the vessel 454 and the receiver 440 about the ball-and-socket joint 452.

The urinal 450 can also have an adapter 430 that further facilitates the adjustability of the receiver 440. The adapter 430 and the ball-and-socket joint 452 can be utilized together to facilitate angular and elevational positioning of the receiver 440 with respect to the vessel 454. The adapter 430 can be positioned between the vessel 454 and the receiver 440, and between the vessel 454 and the ball-and-socket joint 452, to elevate the inlet 466 with respect to the vessel 454. The adapter 430 can comprise a threaded collar 432 that can be threaded to and between the vessel 454 and the shaft 458 of the ball and-socket joint 452. In one aspect, the adapter 430 and the collar 432 can have a handle 480 extending from the collar 432 to facilitate use by either a user or a caretaker.

It is to be understood that the examples set forth herein are not limited to the particular structures, process steps, or materials disclosed, but are extended to equivalents thereof as would be recognized by those ordinarily skilled in the relevant arts. It should also be understood that terminology employed herein is used for the purpose of describing particular examples only and is not intended to be limiting.

Furthermore, the described features, structures, or characteristics may be combined in any suitable manner in one or more examples. In the description, numerous specific details are provided, such as examples of lengths, widths, shapes, etc., to provide a thorough understanding of the technology being described. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the invention in one or more particular applications, it will be apparent to those of ordinary skill in the art that numerous modifications in form, usage and details of implementation can be made without the exercise of inventive faculty, and without departing from the principles and concepts described herein. Accordingly, it is not intended that the invention be limited, except as by the claims set forth below.

What is claimed is:

1. A urine collection and storage system, comprising:
   a) a urinal configured to collect urine, comprising: a vessel with an inlet in a proximal end, a nipple extending from a distal end, and an outlet at the distal end, the inlet being elevated with respect to the outlet and the outlet being substantially flush with an interior bottom of the vessel;
   b) a tube configured to convey urine from the urinal, comprising: a proximal end coupled to the nipple of urinal, and an opposite distal end; and
   c) a collection bag coupled to the distal end of the tube and configured to receive urine from the tube and temporarily store the urine, the collection bag comprising:
   i) a pair of layers joined together about substantially a perimeter to form a lower urine enclosure; and
   ii) the layers joined around substantially an entirety of the lower urine enclosure with a double seal including an outer seal adjacent the perimeter along substantially an entire length of the perimeter and an inner seal spaced-apart from the outer seal.

2. The system in accordance with claim 1, further comprising:
   a) the pair of layers joined together about substantially the perimeter to form an upper hanger pocket, separate from the lower urine enclosure, with a hanger opening therein; and
   b) a hanger coupled to the collection bag and configured to suspend the collection bag pendant therefrom, the hanger comprising a tab disposed in the upper hanger pocket of the collection bag and having a width greater than the hanger opening.

3. The system in accordance with claim 2, wherein the hanger further comprises:
   a) a neck extending from the tab and through the hanger opening;
   b) a front loop receiving the tube therethrough;
   c) a pair of spaced-apart rear loops with a lower loop extending through one of the layers of the collection bag; and
   d) a hook with a vertical column pivotally received in the pair of spaced-apart loops, the hook pivoting between: i) a stored orientation adjacent the hanger, and ii) a use orientation extending outward from the hanger.

4. The system in accordance with claim 1, further comprising:
   a) the vessel having an inclined neck with the inlet in the inclined neck;
   b) a flexible ring substantially circumscribing a perimeter of the inlet;
   c) a handle with a connection end affixed to the inclined neck adjacent the inlet; and
   d) a removable cover disposed on the inlet and the flexible ring of the vessel and comprising:
   i) a front positioned over the inlet and the flexible ring;
   ii) a perimeter wall extending around the front and receiving the inlet and the flexible ring therein;
   iii) an aperture in the perimeter wall to receive the handle; and
   iv) a slit in the perimeter wall from the aperture to an end of the perimeter wall to allow removal of the cover.

5. The system in accordance with claim 1, wherein the urinal is selected from a group of urinals comprising:
   a) a urinal for an adult male comprising an enlarged inlet with a substantially flat, circular opening oriented at an incline between approximately 35-55 degrees;
   b) a urinal for an adult female comprising an enlarged inlet with a concave profile;
   c) a urinal for a juvenile male comprising a reduced inlet with a substantially flat, circular opening oriented at an incline between approximately 35-55 degrees, and comprising a blue color;
   d) a urinal for a juvenile female comprising a reduced inlet with a concave profile, and comprising a pink color;
   e) a urinal for a close-fit male comprising an enlarged inlet with a concave profile; and
   f) a urinal for a slim-fit comprising a narrower inlet and narrower vessel than the adult male and adult female urinals.

6. The system in accordance with claim 1, further comprising:
   a) an intermediate coupler in the tube adjacent to the nipple and bifurcating the tube into separable proximal and distal portions, the intermediate coupler comprising a pair of quick-connect and quick-release tubing couplers; and
   b) the proximal portion of the tube coupled between the nipple and the intermediate coupler and having shorter length and a greater stiffness than the distal portion of the tube coupled between the intermediate coupler and the collection bag and having a longer length and a lesser stiffness than the proximal portion.

7. The system in accordance with claim 6, further comprising:
   a replacement collection bag with a replacement distal tubing portion, configured to replace an existing collection bag with an existing distal tubing portion.

8. The system in accordance with claim 6, wherein a length of the proximal portion of the tube between the nipple and the intermediate coupler is less than 2 inches; and wherein a length of the distal portion of the tube between the intermediate coupler and the collection bag is greater than 36 inches.

9. The system in accordance with claim 6, wherein proximal and distal portions of the tube have substantially a same outer diameter and substantially a same inner diameter.

10. The system in accordance with claim 1, wherein the urinal further comprises:
    a) a flexible ring substantially circumscribing a perimeter of the inlet; and
    b) a smooth annular bead of adhesive between the flexible ring and the urinal.

11. The system in accordance with claim 1, further comprising:

a) the vessel having an inclined neck with the inlet in the inclined neck;
b) a flexible ring substantially circumscribing a perimeter of the inlet;
c) a handle with a connection end affixed to the inclined neck adjacent the inlet; and
d) a removable cover disposed on the inlet and the flexible ring of the vessel and comprising:
  i) a front positioned over the inlet and the flexible ring;
  ii) a perimeter wall extending around the front and receiving the inlet and the flexible ring therein;
  iii) an aperture in the perimeter wall to receive the handle; and
  iv) a slit in the perimeter wall from the aperture to an end of the perimeter wall to allow removal of the cover.

12. A urine collection and storage system, comprising:
a) a urinal configured to collect urine, comprising: a vessel with an inlet in a proximal end, a nipple extending from a distal end, and an outlet at the distal end, the inlet being elevated with respect to the outlet and the outlet being substantially flush with an interior bottom of the vessel;
b) a tube configured to convey urine from the urinal, comprising: a proximal end coupled to the nipple of urinal, and an opposite distal end;
c) a collection bag coupled to the distal end of the tube and configured to receive urine from the tube and temporarily store the urine, the collection bag comprising:
  i) a pair of layers joined together about substantially a perimeter to form a lower urine enclosure; and
  ii) the layers joined around substantially an entirety of the lower urine enclosure with a double seal including an outer seal adjacent the perimeter along substantially an entire length of the perimeter and an inner seal spaced-apart from the outer seal;
d) the pair of layers joined together about substantially the perimeter to form an upper hanger pocket, separate from the lower urine enclosure, with a hanger opening therein; and
e) a hanger coupled to the collection bag and configured to suspend the collection bag pendant therefrom, the hanger comprising a tab disposed in the upper hanger pocket of the collection bag and having a width greater than the hanger opening.

13. The system in accordance with claim 12, wherein the hanger further comprises:
a) a neck extending from the tab and through the hanger opening;
b) a front loop receiving the tube therethrough;
c) a pair of spaced-apart rear loops with a lower loop extending through one of the layers of the collection bag; and
d) a hook with a vertical column pivotally received in the pair of spaced-apart loops, the hook pivoting between:
  i) a stored orientation adjacent the hanger, and ii) a use orientation extending outward from the hanger.

14. The system in accordance with claim 12, further comprising:
a) the vessel having an inclined neck with the inlet in the inclined neck;
b) a flexible ring substantially circumscribing a perimeter of the inlet;
c) a handle with a connection end affixed to the inclined neck adjacent the inlet; and
d) a removable cover disposed on the inlet and the flexible ring of the vessel and comprising:
  i) a front positioned over the inlet and the flexible ring;
  ii) a perimeter wall extending around the front and receiving the inlet and the flexible ring therein;
  iii) an aperture in the perimeter wall to receive the handle; and
  iv) a slit in the perimeter wall from the aperture to an end of the perimeter wall to allow removal of the cover.

15. The system in accordance with claim 12, wherein the urinal is selected from a group of urinals comprising:
a) a urinal for an adult male comprising an enlarged inlet with a substantially flat, circular opening oriented at an incline between approximately 35-55 degrees;
b) a urinal for an adult female comprising an enlarged inlet with a concave profile;
c) a urinal for a juvenile male comprising a reduced inlet with a substantially flat, circular opening oriented at an incline between approximately 35-55 degrees, and comprising a blue color;
d) a urinal for a juvenile female comprising a reduced inlet with a concave profile, and comprising a pink color;
e) a urinal for a close-fit male comprising an enlarged inlet with a concave profile; and
f) a urinal for a slim-fit comprising a narrower inlet and narrower vessel than the adult male and adult female urinals.

16. The system in accordance with claim 12, further comprising:
a) an intermediate coupler in the tube adjacent to the nipple and bifurcating the tube into separable proximal and distal portions, the intermediate coupler comprising a pair of quick-connect and quick-release tubing couplers; and
b) the proximal portion of the tube coupled between the nipple and the intermediate coupler and having shorter length and a greater stiffness than the distal portion of the tube coupled between the intermediate coupler and the collection bag and having a longer length and a lesser stiffness than the proximal portion.

17. The system in accordance with claim 16, further comprising:
a replacement collection bag with a replacement distal tubing portion, configured to replace an existing collection bag with an existing distal tubing portion.

18. The system in accordance with claim 12, wherein the urinal further comprises:
a) a flexible ring substantially circumscribing a perimeter of the inlet; and
b) a smooth annular bead of adhesive between the flexible ring and the urinal.

19. The system in accordance with claim 12, further comprising:
a) the vessel having an inclined neck with the inlet in the inclined neck;
b) a flexible ring substantially circumscribing a perimeter of the inlet;
c) a handle with a connection end affixed to the inclined neck adjacent the inlet; and
d) a removable cover disposed on the inlet and the flexible ring of the vessel and comprising:
  i) a front positioned over the inlet and the flexible ring;
  ii) a perimeter wall extending around the front and receiving the inlet and the flexible ring therein;
  iii) an aperture in the perimeter wall to receive the handle; and iv) a slit in the perimeter wall from the aperture to an end of the perimeter wall to allow removal of the cover.

20. A urine collection and storage system, comprising:
a) a urinal configured to collect urine, comprising:
   i) a vessel with an inclined neck at a proximal end, an inlet in the inclined neck at the proximal end, a nipple extending from a distal end, and an outlet at the distal end, the inlet being elevated with respect to the outlet and the outlet being substantially flush with an interior bottom of the vessel;
   ii) a handle with a connection end affixed to the inclined neck adjacent the inlet and extending to a free end with a grip portion of the handle disposed over the vessel;
   iii) a flexible ring substantially circumscribing a perimeter of the inlet, the flexible ring formed of closed cell foam; and
   iv) a smooth annular bead of adhesive between the flexible ring and the urinal;
b) a removable cover disposed on the inlet and the flexible ring of the vessel and comprising:
   i) a front positioned over the inlet and the flexible ring;
   ii) a perimeter wall extending around the front and receiving the inlet and the flexible ring therein;
   iii) an aperture in the perimeter wall to receive the handle; and
   iv) a slit in the perimeter wall from the aperture to an end of the perimeter wall to allow removal of the cover;
c) a tube configured to convey urine from the urinal, comprising:
   i) a proximal end coupled to the nipple of the urinal;
   ii) an opposite distal end; and
   iii) an intermediate coupler in the tube adjacent to the nipple and bifurcating the tube into separable proximal and distal portions, the intermediate coupler comprising a pair of quick-connect and quick-release tubing couplers;
d) a collection bag coupled to the distal end of the tube and configured to receive urine from the tube and temporarily store the urine, the collection bag comprising:
   i) a pair of layers joined together about substantially a perimeter to form a lower urine enclosure and an upper hanger pocket, separate from the lower urine enclosure, with a hanger opening therein;
   ii) the layers joined around substantially an entirety of the lower urine enclosure with a double seal including an outer seal adjacent the perimeter along substantially an entire length of the perimeter and an inner seal spaced-apart from the outer seal; and
   iii) a hanger coupled to the collection bag and configured to suspend the collection bag pendant therefrom, the hanger comprising a tab disposed in the upper hanger pocket of the collection bag and having a width greater than the hanger opening; and
e) the proximal portion of the tube coupled between the nipple and the intermediate coupler and having a shorter length and a greater stiffness than the distal portion of the tube coupled between the intermediate coupler and the collection bag and having a longer length and a lesser stiffness than the proximal portion.

* * * * *